US009603621B2

(12) United States Patent
Zhou

(10) Patent No.: US 9,603,621 B2
(45) Date of Patent: Mar. 28, 2017

(54) LOW-RESISTANCE GENERAL SEALING APPARATUS FOR TROCAR, AND TROCAR

(75) Inventor: Xing Zhou, Guangzhou (CN)

(73) Assignee: GUANGZHOU T. K. MEDICAL INSTRUMENT CO., LTD., Guangzhou, Guandong (CN)

( * ) Notice: Subject to any disclaimer, the term of this patent is extended or adjusted under 35 U.S.C. 154(b) by 674 days.

(21) Appl. No.: 13/993,635

(22) PCT Filed: Dec. 11, 2011

(86) PCT No.: PCT/CN2011/083795
§ 371 (c)(1),
(2), (4) Date: Jun. 12, 2013

(87) PCT Pub. No.: WO2012/079491
PCT Pub. Date: Jun. 21, 2012

(65) Prior Publication Data
US 2013/0261651 A1    Oct. 3, 2013

(30) Foreign Application Priority Data

Dec. 14, 2010 (CN) .......................... 2010 1 0588098

(51) Int. Cl.
*A61B 17/34* (2006.01)
(52) U.S. Cl.
CPC .......... *A61B 17/34* (2013.01); *A61B 17/3421* (2013.01); *A61B 17/3462* (2013.01); *A61B 2017/349* (2013.01); *A61B 2017/3464* (2013.01)
(58) Field of Classification Search
CPC . A61B 17/3421; A61B 17/34; A61B 17/3462; A61B 17/349; A61B 2017/3464
See application file for complete search history.

(56) References Cited

U.S. PATENT DOCUMENTS

| 5,342,315 A | 8/1994 | Rowe et al. |
| 5,391,153 A | 2/1995 | Haber et al. |
| (Continued) | | |

FOREIGN PATENT DOCUMENTS

| CN | 101138662 A | 3/2008 |
| CN | 101474089 A | 7/2009 |
| (Continued) | | |

OTHER PUBLICATIONS

Zhou, Grant Certificate, EP11849246.1, Jul. 20, 2016, 1 pg.
(Continued)

*Primary Examiner* — Richard Louis
(74) *Attorney, Agent, or Firm* — Morgan, Lewis & Bockius LLP

(57) ABSTRACT

Disclosed are a low-resistance general sealing apparatus for a trocar and a trocar. A sealing ring (3) is compressed between an upper guiding mechanism (1) and a lower guiding mechanism (2). A smooth transition between the upper guiding mechanism (1) and the lower guiding mechanism (2) minimizes the contact area between the sealing ring (3) and a surgical instrument, which not only provides a guiding function when different forms of surgical instrument are inserted or removed, but also maximally transforms a "soft-hard" friction area between the sealing ring (3) and the surgical instrument into a "hard-hard" friction area between the plastics of upper and lower guiding mechanisms and an outer metal sheath of the surgical instrument, thereby greatly reducing the motion resistance, and meanwhile, having an excellent sealing effect. The sealing apparatus and the trocar are also applicable to instruments with diameters between 5 mm and 12 mm.

20 Claims, 16 Drawing Sheets

(56) References Cited

U.S. PATENT DOCUMENTS

| | | | |
|---|---|---|---|
| 5,542,931 A | 8/1996 | Gravener et al. | |
| 5,814,026 A | 9/1998 | Yoon | |
| 6,569,120 B1* | 5/2003 | Green | A61B 17/34 137/849 |
| 2003/0195541 A1* | 10/2003 | Exline | A61B 17/3462 606/185 |
| 2004/0106942 A1 | 6/2004 | Taylor et al. | |
| 2005/0113757 A1* | 5/2005 | McFarlane | A61B 17/3498 604/167.03 |
| 2006/0135978 A1* | 6/2006 | Franer | A61B 17/3462 606/185 |
| 2008/0171987 A1* | 7/2008 | Franer | A61B 17/3462 604/167.03 |
| 2009/0234293 A1 | 9/2009 | Albrecht et al. | |
| 2009/0240204 A1* | 9/2009 | Taylor | A61B 17/3462 604/167.03 |
| 2010/0016799 A1 | 1/2010 | Schweitzer et al. | |
| 2010/0022957 A1 | 1/2010 | Sauer et al. | |
| 2010/0194060 A1* | 8/2010 | Blanco | A61B 17/34 277/650 |
| 2010/0249711 A1* | 9/2010 | Fischvogt | A61B 17/3462 604/167.03 |
| 2011/0237901 A1* | 9/2011 | Duke | A61B 17/3462 600/208 |
| 2013/0138086 A1* | 5/2013 | Thor | A61M 39/10 604/535 |

FOREIGN PATENT DOCUMENTS

| | | |
|---|---|---|
| CN | 101505665 A | 8/2009 |
| WO | WO 93/01850 A1 | 2/1993 |

OTHER PUBLICATIONS

Zhou, Office Action, CN201010588098.9, Dec. 24, 2014, 5 pgs.
Zhou, Invitation to File a Search Results or a Statement of Non-Availability Pursuant to Rule 70b(1) EPC, EP11849246.1, Nov. 18, 2015, 1 pg.
Zhou, Communication Pursuant to Rules 70(2) and 70a(2) EPC, 11849246.1, Apr. 29, 2015, 1 pg.
Zhou, Extended EP Search Report EP11849246.1, Apr. 10, 2015, 4 pgs.
Zhou, Communication Pursuant to Rule 71(3) Intention to Grant, EP11849246.1, Jan. 29, 2016, 7 pgs.
Zhou, Decision to Grant a European Patent, EP11849246.1, Jun. 23, 2016, 2 pgs.
Xing Zhou, International Search Report, PCT/CN2011/083795, Mar. 15, 2012, 4 pgs.

* cited by examiner

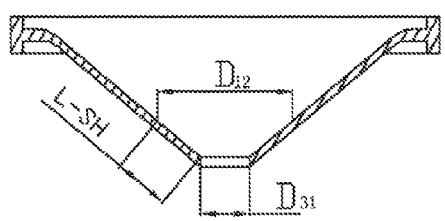
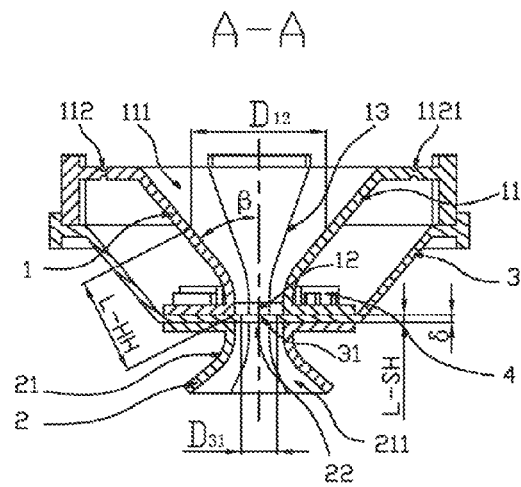
FIG. 1-1
FIG. 2-1
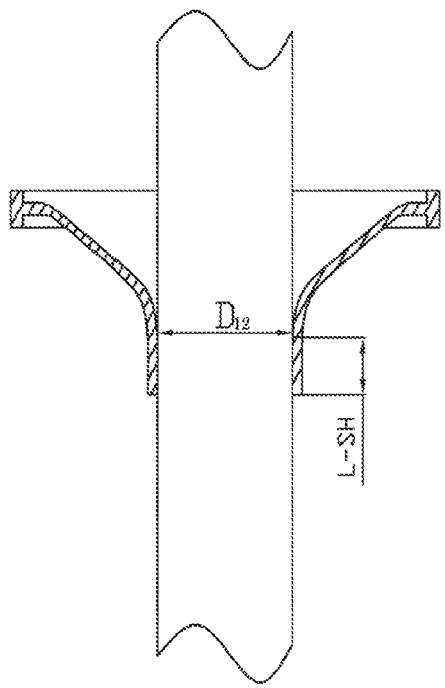
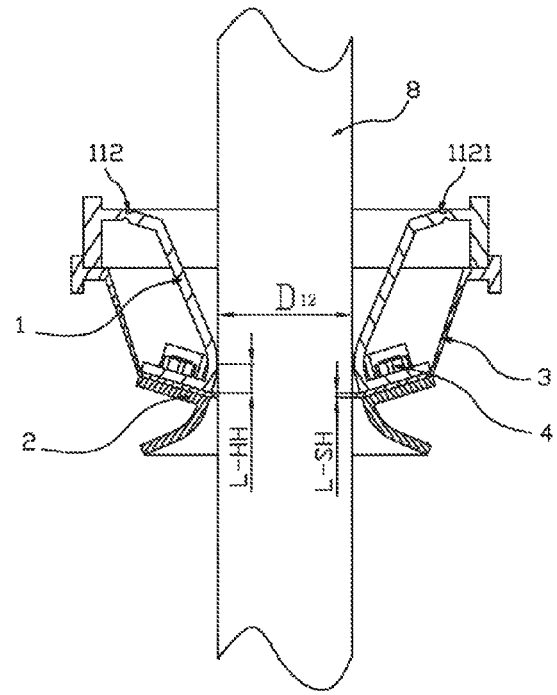
FIG. 1-2
FIG. 2-2

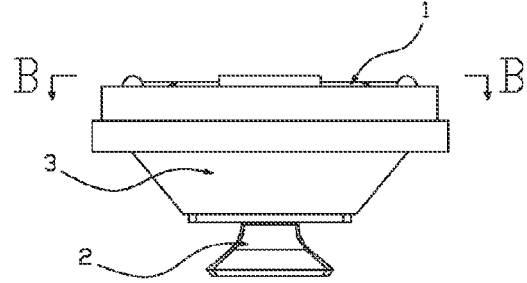
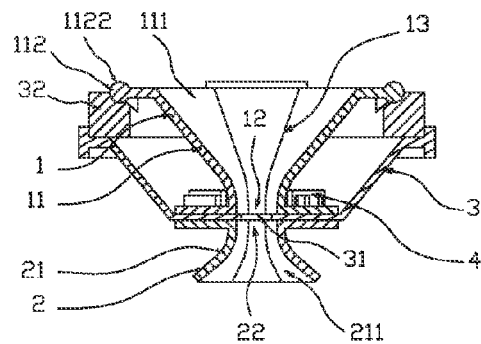
FIG. 3-1    FIG. 3-2
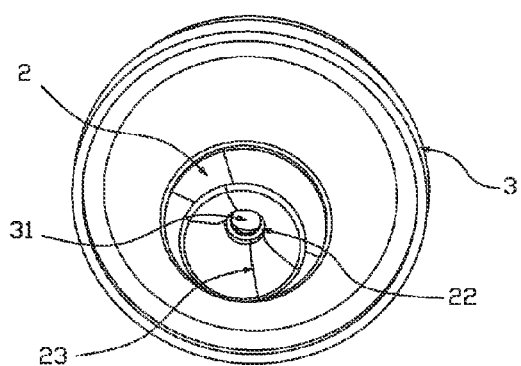
FIG. 3-3

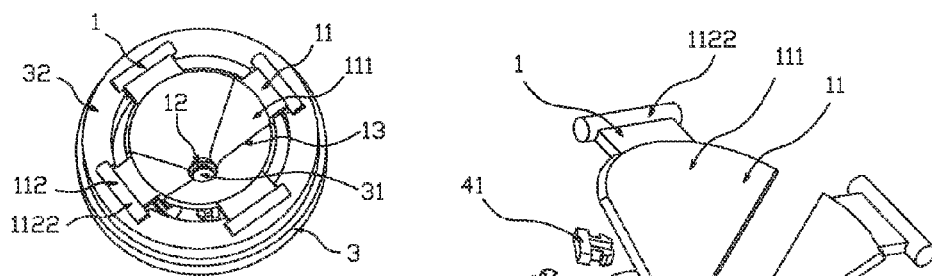
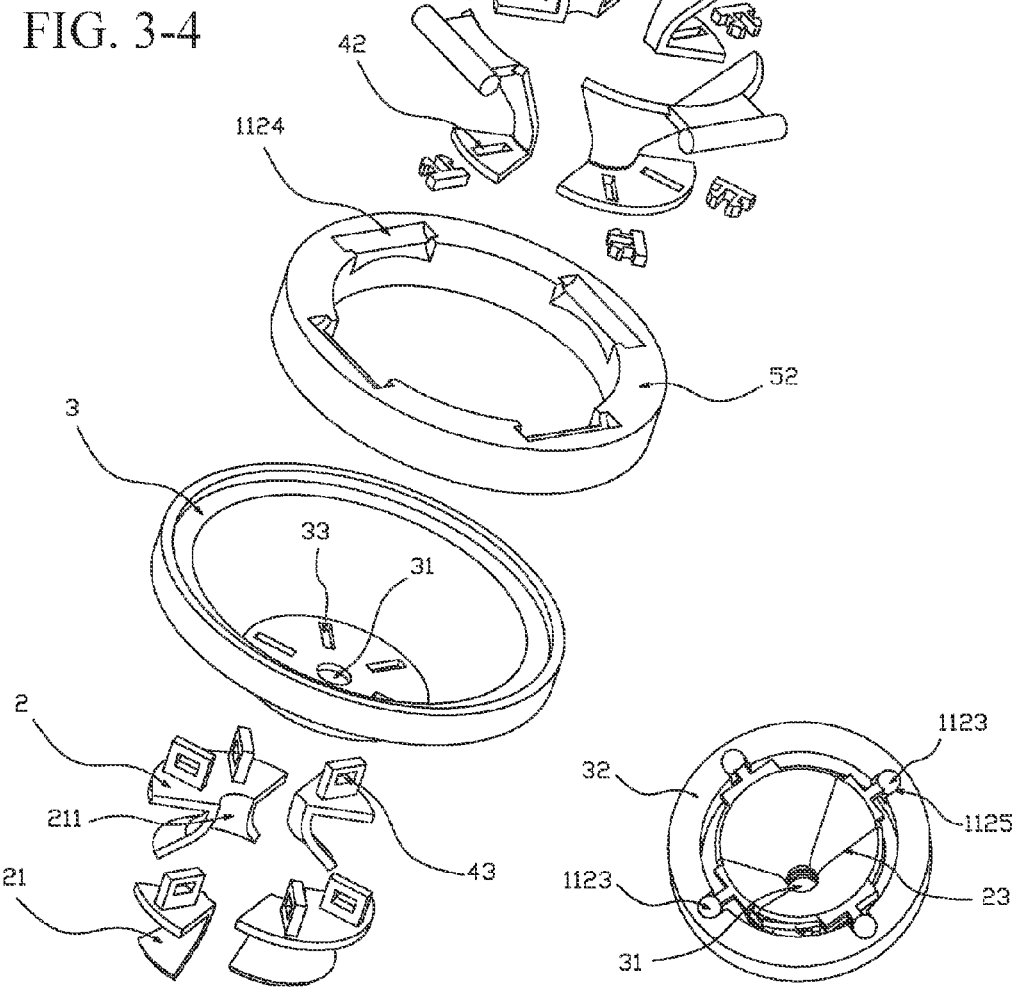
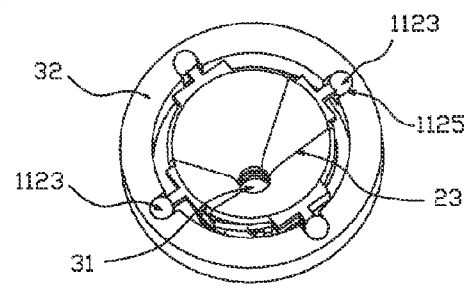
FIG. 3-4
FIG. 3-5
FIG. 3-6

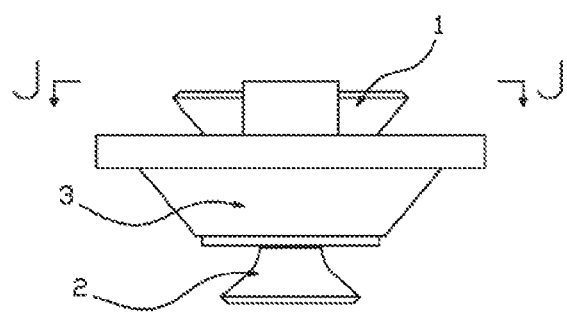
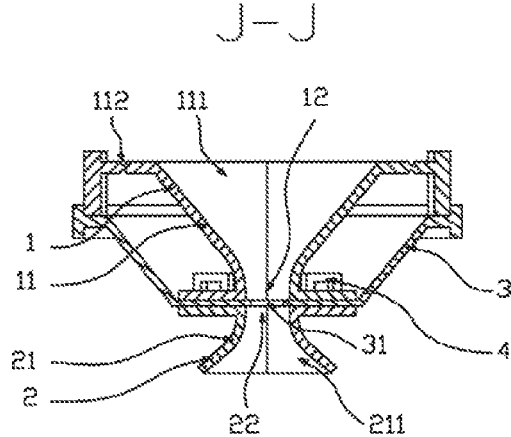
FIG. 8-1
FIG. 8-2
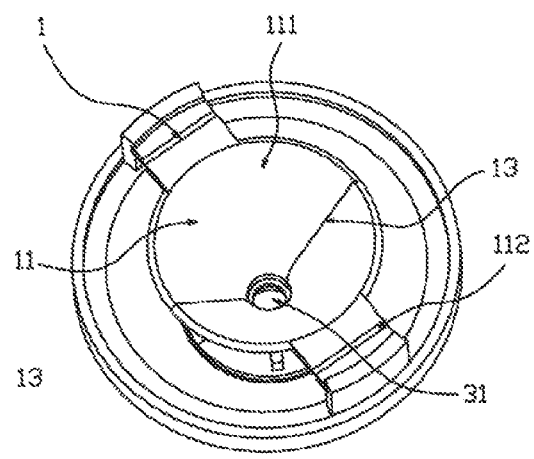
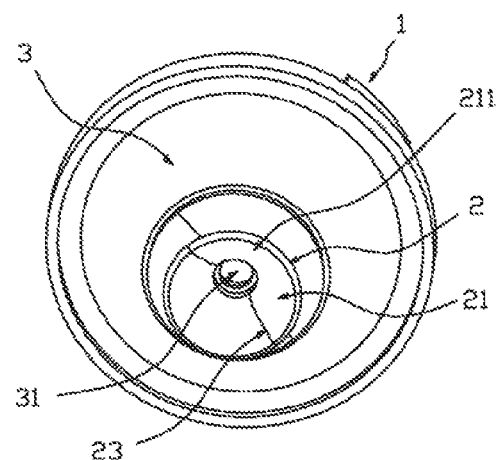
FIG. 8-3
FIG. 8-4

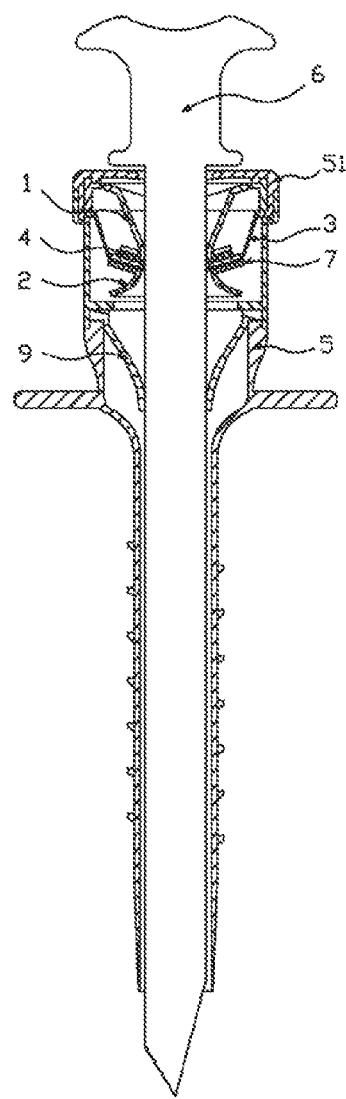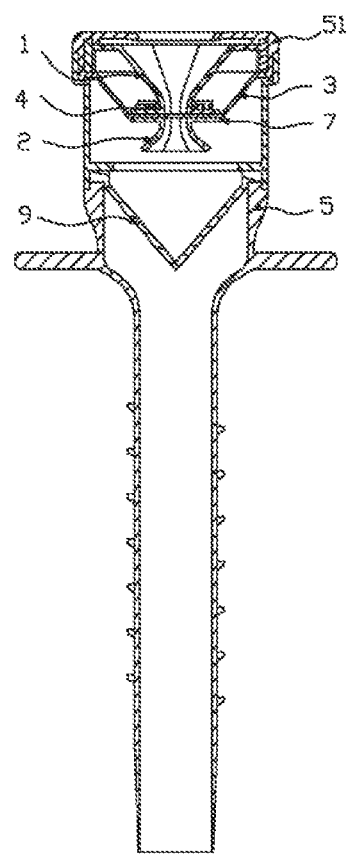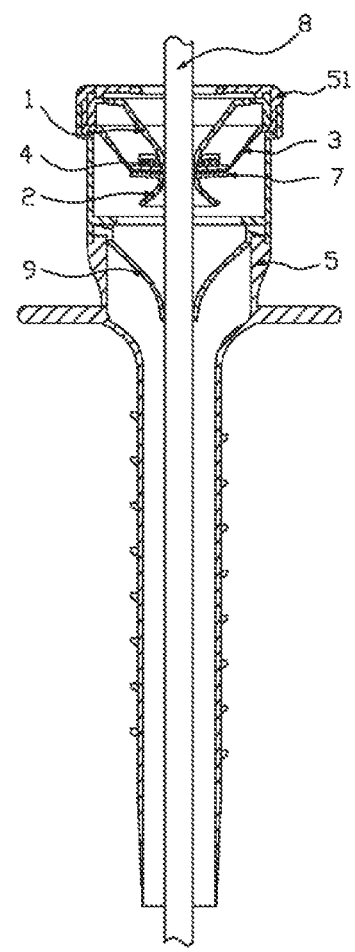
FIG. 12-1  FIG. 12-2  FIG. 12-3

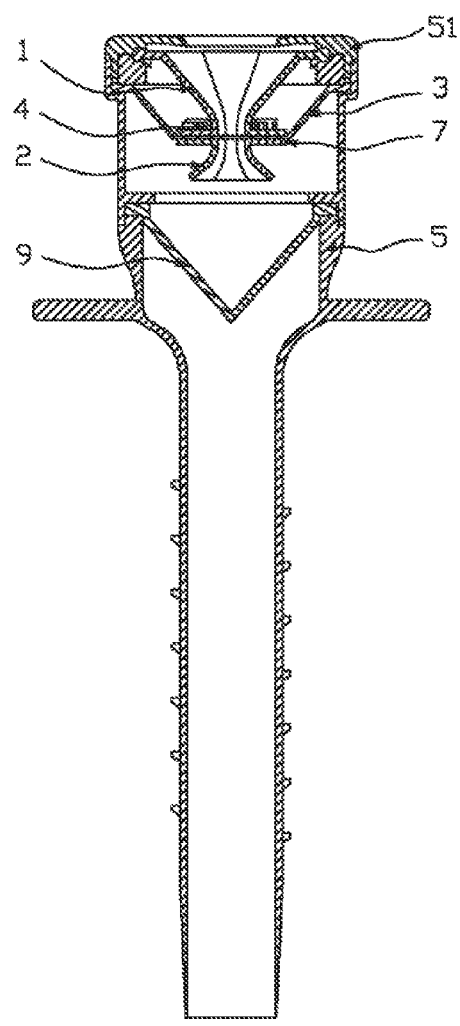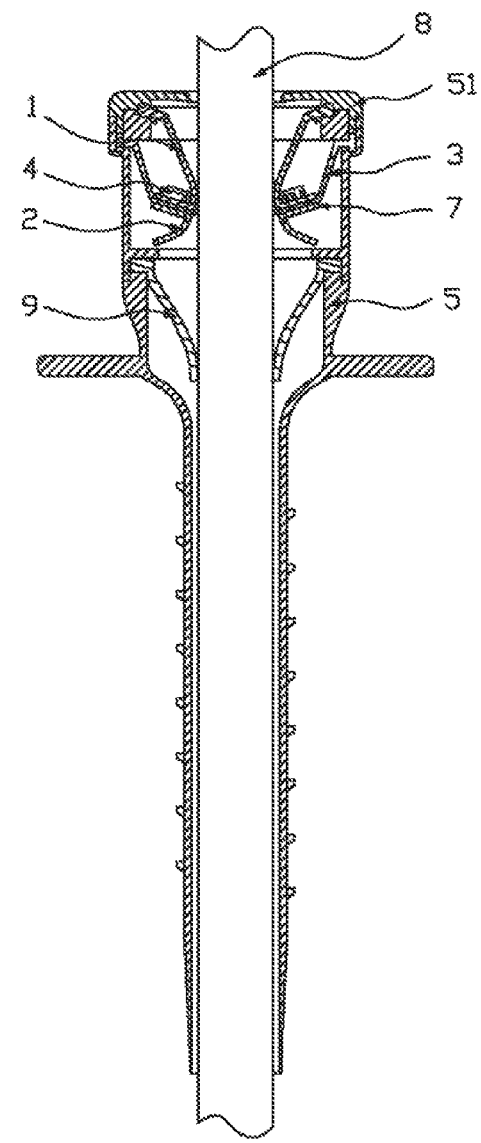
FIG. 13-1  FIG. 13-2

LOW-RESISTANCE GENERAL SEALING APPARATUS FOR TROCAR, AND TROCAR

CROSS REFERENCE TO RELATED APPLICATIONS

This Application is a United States National Stage Application filed under 35 U.S.C. §371 of PCT Patent Application Serial No. PCT/CN2011/083795 filed on Dec. 11, 2011, which claims the benefit of and priority to Chinese Patent Application No. 201010588098.9 filed on Dec. 14, 2010, both of which are hereby incorporated by reference in their entireties.

TECHNICAL FIELD

The disclosed implementations relate generally to medical instrument, and in particular, to a sealing apparatus of a trocar used in a laparoscopic surgery and a trocar using the sealing apparatus.

BACKGROUND

A laparoscopic surgery is applied more and more widely. In order to avoid iatrogenic infection, the consumption of a disposable trocar used in the laparoscopic surgery is increasingly greater. The trend of simplifying the structure, reducing the cost, improving the performance on the basis of ensuring using performance has already become an improvement direction of the trocar.

In the prior art, a sealing structure of the trocar is formed by a radial sealing ring and a check valve. A common check valve, namely, an axial sealing apparatus has two types. One type is a spring pressed structure, forming sealing by a spring leaf pushing a flapper to oppress a silica gel sealing ring. The check valve is formed by the spring leaf, the flapper and the silica gel sealing ring, the spring leaf and the flapper are generally made of stainless steel, the form of the sealing ring is usually used in a metal-made reusable trocar, and the trocar is expensive and has a heavy weight. In recent years, in order to adapt to the development requirement of the disposable trocar, a funnel-shaped silica gel sealing ring is developed. The funnel-shaped silica gel sealing ring has a straight through notch provided at the bottom of the funnel, and achieves the sealing effect by means of the contractility of the silica gel and the pressure formed by carbon dioxide pneumoperitoneum during use. The funnel-shaped silica gel sealing ring is generally widely applied in the disposable trocar. The radial sealing ring generally adopts a funnel-shaped structure with a central hole and the sealing ring easily leaks when a surgical instrument shakes, having a poor dynamic sealing effect. Additionally, when a 10 mm or 12 mm surgical instrument is inserted in a medical silica gel sealing ring with the diameter being 4 mm, the resistance of the surgical instrument in reciprocating motion is also large, which brings inconvenience to a surgical operation of a surgeon.

Additionally, surgical instruments have heads in different shapes. Particularly, a surgical instrument, such as a titanium clamp, has a V-shaped head splayed when being delivered to the abdominal cavity through the trocar, and generally cannot pass through the funnel-shaped silica gel sealing ring in the prior art. Another defect of the V-shaped funnel-shaped silica gel sealing ring is that a surgical instrument whose head has a groove or raised steps, such as a harmonic scalpel, is easy to get stuck when the surgical instrument is removed, so the motion is not smooth.

Therefore, the radial sealing apparatus of the existing trocar needs to be improved, so as to achieve the purpose of not only using a 10 mm instrument on a trocar whose diameter is 10 mm, but also using surgical instruments with diameters between 5 mm and 10 mm; and not only using a 12 mm instrument on a trocar whose diameter is 12 mm, but also using surgical instruments with diameters between 5 mm and 12 mm, thereby being general. Meanwhile, the radial sealing apparatus of the improved trocar can be adapted to various surgical instruments in different shapes, thereby facilitating insertion and removal of the instrument, with low resistance and smooth motion. Evidently, the sealing apparatus and the trocar in the prior art cannot satisfy the requirements, thus requiring improvement.

SUMMARY

The present invention is directed to a sealing ring apparatus for a trocar and a trocar using the sealing apparatus, which are capable of using instruments with diameters between 5 mm and 12 mm, thus having generality, desirable sealing effect, and low resistance when a surgical instrument moves back and forth.

The core of technical solutions of the present invention lies in that:

A sealing ring is compressed between an upper guiding mechanism and a lower guiding mechanism, and a smooth transition between the upper guiding mechanism and the lower guiding mechanism minimizes the contact area between the sealing ring and the surgical instrument. The design of the technical solution not only provides a guiding function when an instrument is inserted or removed, being applicable to the insertion and removal of all forms of the surgical instrument; but also maximally transforming a "soft-hard" friction area between the sealing ring and the surgical instrument into a "hard-hard" friction area between the plastics of upper and lower guiding mechanisms and an outer metal sheath of the surgical instrument, thereby greatly reducing the motion resistance of the surgical instrument in the sealing apparatus and the trocar.

The low-resistance general sealing apparatus of the present invention is implemented as follows.

A low-resistance general sealing apparatus for a trocar is provided. The sealing apparatus is provided with an upper guiding mechanism, a lower guiding mechanism, a sealing ring, and a connection locking mechanism, where the upper guiding mechanism is provided with two or more upper sliders, a funnel-shaped structure having a large upper part and a small lower part is formed between the upper sliders, and the upper slider is provided with a guiding surface; the lower guiding mechanism is provided with two or more lower sliders, an inverted funnel-shaped structure having a small upper part and a large lower part is formed between the lower sliders, and the lower slider is provided with a guiding surface; the sealing ring is made of an elastic medical macromolecular material and is provided with a surgical instrument through hole; the connection locking mechanism is a concave-convex matching structure; the connection locking mechanism connects the upper guiding mechanism and the lower guiding mechanism together fixedly, the sealing ring is placed between the upper guiding mechanism and the lower guiding mechanism; a smooth transition is formed between the upper sliders and the corresponding lower sliders; the diameter of the surgical instrument through hole in the sealing ring is smaller than the diameter of a lower through hole of the upper guiding mechanism and the diameter of an upper through hole of the lower guiding mechanism.

Furthermore, the connection locking mechanism connects the upper guiding mechanism and the lower guiding mechanism together fixedly through the concave-convex matching mechanism; or the connection locking mechanism connects the upper guiding mechanism and the lower guiding mechanism together fixedly through the concave-convex match structure by means of the heat seal or welding technique; or, the connection locking mechanism connects the upper guiding mechanism and the lower guiding mechanism together fixedly through the concave-convex matching structure by applying a chemical binder to the upper guiding mechanism (1) and the lower guiding mechanism (2).

When a surgical instrument is inserted, the upper sliders of the upper guiding mechanism splay outward, the gap between the upper sliders enlarges; and meanwhile, the lower sliders of the lower guiding mechanism are driven to splay outward, and the gap between the lower sliders enlarges.

When a surgical instrument is removed, under the effect of elastic resilience of the sealing ring, the upper sliders of the upper guiding mechanism contract inward, the gap between the upper sliders decreases; and meanwhile, the lower sliders of the lower guiding mechanism are driven to contract inward and the gap between the lower sliders decreases. When the surgical instrument is completely removed, the surgical instrument through hole of the sealing ring restores to the initial position, and meanwhile, the upper sliders of the upper guiding mechanism and the lower sliders of the lower guiding mechanism also restore to the initial position.

The upper guiding mechanism is provided with a dynamic connection mechanism.

Furthermore, the dynamic connection mechanism refers to a low-resistance area formed by a groove or elastic material that easily deforms under an external force and restores its original shape after the external force of deformation is removed; or, the dynamic connection mechanism refers to a movable spherical or axial limit rotation mechanism.

The diameter of the lower through hole of the funnel-shaped structure having a large upper part and a small lower part formed between the upper sliders is close or equal to the diameter of an upper through hole of the inverted funnel-shaped structure having a small upper part and a large lower part formed between the lower sliders.

Generally, the size difference between the diameter of the lower through hole of the upper guiding mechanism and the diameter the upper through hole of the lower guiding mechanism is smaller than ±1.5 mm. Both the diameter of the lower through hole of the upper guiding mechanism and the diameter of the upper through hole of the lower guiding mechanism are greater than the diameter of the surgical instrument through hole of the sealing ring by 1 mm to 6 mm, and preferably, by 1.5 mm to 4 mm.

A preferred structure of the upper guiding mechanism is a 4-segment funnel-shaped structure having a large upper part and a small lower part and formed by 4 upper sliders; and a preferred structure of the lower guiding mechanism is a 4-segment inverted funnel-shaped structure having a small upper part and a large lower part and formed by 4 lower sliders matched with the upper sliders.

Furthermore, in the 4 upper sliders forming the upper guiding mechanism, 2 upper sliders whose area of the guiding surface is greater form a pair of primary guiding gliders, the rest 2 upper sliders whose area of the guiding surface is smaller form a pair of auxiliary guiding gliders, and the primary guiding gliders and the auxiliary guiding gliders have different colors. The primary guiding gliders are generally used to guide the splayed surgical instrument, for example, inserting a titanium clamp equipped with a titanium clip. The primary guiding gliders are generally blue or green; and the auxiliary guiding gliders are white or black.

Ultra smooth material coating is arranged on the guiding surface of the upper guiding mechanism and the guiding surface (211) of the lower guiding mechanism. The ultra smooth material coating is generally made of a hydrophilic material and may also be made of a material with a self-lubricating function.

The upper sliders of the upper guiding mechanism and the lower sliders of the lower guiding mechanism are generally made of a hydrophilic material and may also be made of a material with a self-lubricating function.

The sealing ring is a sealing ring having a trapezoidal, quasi-trapezoidal, V-shaped, and approximately H-shaped cross section, where the trapezoidal or quasi-trapezoidal sealing ring is preferred.

Furthermore, when the sealing ring is a sealing ring having a trapezoidal or quasi-trapezoidal cross section, the diameter $D_{31}$ of the surgical instrument through hole is between 1 mm and 5 mm, and preferably between 2.5 mm and 4.5 mm; the diameter $D_{32}$ of the bottom of the trapezoidal sealing ring is between 3 mm and 40 mm, and preferably between 10 mm and 30 mm; and the thickness $\delta$ of the bottom of the trapezoidal sealing ring is between 0.05 mm and 1.5 mm, and preferably between 0.3 mm and 0.9 mm.

The wall thickness of the sealing ring is non-equal. Generally, the wall thickness of the sealing ring is greater in the upper part and smaller in the lower part.

The angle $\beta$ between the guiding surface of the upper guiding mechanism and a central shaft of the funnel-shaped structure is between 80° and 10°, and preferably between 50° and 15°.

Furthermore, the sealing ring is provided with a buffering ring, and the buffering ring is of a wrinkle structure. The buffering ring is generally disposed at the upper part of the sealing ring.

The upper guiding mechanism may further be fixed at the upper side of the sealing ring through the concave-convex structure.

The sealing apparatus is provided with a positioning block used to fix the sealing ring and/or the dynamic connection mechanism of the upper guiding mechanism. When the positioning block is used to fix the dynamic connection mechanism of the upper guiding mechanism on the upper side of the sealing ring, the dynamic connection mechanism and the positioning block are fixed together, so the upper side of the sealing ring is compressed fixedly between the dynamic connection mechanism and the positioning block; the upper edge of the sealing ring is provided with the buffering ring, so the upper guiding mechanism, the lower guiding mechanism and the surgical instrument through hole of the sealing ring can perform 2-dimensional translational motion together along the horizontal direction, thereby satisfying different motion requirements of surgical operations.

The lower side of the lower slider of the lower guiding mechanism is provided with a traction plate, and the traction plate is made of an elastic medical macromolecular material selected from medical silica gel, medical rubber, medical polyurethane, medical latex, and a combination thereof. The traction plate has a traction effort on the lower sliders of the lower guiding mechanism when the surgical instrument is removed, and the elastic resilience is also conducive to the restoration of the lower gliders after the surgical instrument is completely removed; and meanwhile, the traction plate is soft and does not affect the motion of splaying outward of the lower sliders when the surgical instrument is inserted.

Furthermore, the sealing ring is made of an elastic medical macromolecular material.

The medical flexible macromolecule material is selected from medical silica gel, medical rubber, medical polyurethane, medical latex, and a combination thereof.

The guiding mechanism, the lower guiding mechanism and the connection locking mechanism are made of medical macromolecular materials or medical metal materials that are selected from: medical macromolecular materials such as medical PU, PP, PA, PE, PC, or medical metal materials such as medical stainless steel, medical titanium and titanium alloy, medical TiNi shape memory alloy and TiZrNb alloy.

The present invention further provides a trocar.

The trocar includes the low-resistance general sealing apparatus for a trocar of the present invention.

Furthermore, the low-resistance general sealing apparatus of the present invention is mounted at a housing or a positioning block of a sheath of the trocar through the dynamic connection mechanism.

The radial sealing of the trocar adopts the low-resistance general sealing apparatus of the present invention, and the axial sealing adopts a funnel-shaped straight sealing ring.

The radial sealing of the trocar adopts a low-resistance general sealing apparatus of the present invention, and the axial sealing adopts a flipping-type sealing apparatus.

The radial sealing of the trocar adopts the low-resistance general sealing apparatus of the present invention, and the axial sealing adopts a spherical sealing apparatus.

A sealing ring of the trocar is generally made of a medical elastic material, commonly medical silica gel, while the surgical instrument is generally made of metal or plastic. When the surgical instrument made of metal or plastic moves in the medical silica gel, the frictional resistance is large, while the frictional resistance between metal and plastic is small.

The present invention adopts a structure of compressing the sealing ring between the upper guiding mechanism and the lower guiding mechanism and minimizing the contact area between the sealing ring and the surgical instrument through the smooth transition between the upper guiding mechanism and the lower guiding mechanism, which not only provides a guiding function when the instrument is inserted or removed, being applicable to the insertion and removal of all forms of the surgical instruments; but also maximally transforms a "soft-hard" friction area between the sealing ring and the surgical instrument into a "hard-hard" friction area between the plastic of upper and lower guiding surfaces and the outer metal sheath of the surgical instrument, thereby greatly reducing the motion resistance of the surgical instrument in the sealing apparatus and the trocar. Meanwhile, the sealing apparatus and the trocar of the present invention are applicable to surgical instruments with diameters between 5 mm and 12 mm to implement the generality, with excellent sealing effect and low motion resistance.

Additionally, the lower guiding mechanism of the sealing apparatus of the present invention not only has the guiding function, but also can prevent turnover of the sealing ring when the surgical instrument is withdrawn outward. The turnover of the sealing ring greatly increases the resistance of the withdrawing of the surgical instrument, and the sealing apparatus of the present invention effectively avoids the turnover phenomenon.

By means of the sealing apparatus of the present invention, surgical instruments with diameters between 12 mm and 5 mm can freely insert in the sealing apparatus, while maintaining excellent dynamic sealing performance. The sealing apparatus and the trocar of the present invention can further implement free changing of the surgical instruments with diameters between 5 mm and 15 mm while maintaining low motion resistance.

BRIEF DESCRIPTION OF DRAWINGS

The aforementioned implementation of the invention as well as additional implementations will be more clearly understood as a result of the following detailed description of the various aspects of the invention when taken in conjunction with the drawings. Like reference numerals refer to corresponding parts throughout the several views of the drawings.

FIG. 1-1 is a schematic structural diagram of a general sealing ring in the prior art.

In FIG. 1-1, $D_{31}$ is the diameter of a surgical instrument through hole of a sealing ring, $D_{12}$ is the position of an arc with the diameter being 12 mm, and L-SH represents the length of a "soft-hard" friction area formed between a silica gel sealing ring and an outer metal sheath of a surgical instrument after a 12 mm surgical instrument is inserted.

FIG. 1-2 is a schematic structural diagram of the sealing ring after the surgical instrument is inserted in FIG. 1-1.

FIG. 2-1 is a schematic structural diagram of a 4-segment low-resistance general sealing apparatus according to the present invention.

FIG. 2-1 is also an A-A sectional view of FIG. 2-3. In FIG. 2-1, $D_{31}$ is the diameter of a surgical instrument through hole 31 of the sealing ring, $D_{12}$ is the position of an arc with the diameter being 12 mm, L-SH represents the length of a "soft-hard" friction area formed between a silica gel sealing ring 3 and an outer metal sheath of a surgical instrument 8 after a 12 mm surgical instrument is inserted, and L-HH represents the length of a "hard-hard" friction area formed between the plastics of a guiding surface 111 of an upper slider 11 and an outer metal sheath of a surgical instrument 8 after a 12 mm surgical instrument is inserted.

FIG. 2-2 is an operation principle diagram of the 4-segment low-resistance general sealing apparatus according to the present invention in FIG. 2-1.

In FIG. 2-2, a dynamic connection mechanism 112 of an upper guiding mechanism 1 is implemented through an elastic weak-intensity area disposed on the upper side of the upper guiding mechanism 1 and formed through a groove 1121. Because the groove 1121 forms the elastic weak-intensity area, the intensity at the area is low and the area is easy to deform. After the surgical instrument 8 is inserted, the groove 1121 deforms and drives upper sliders 11, lower sliders 22 and a sealing ring 3 to splay outward to facilitate the inserting of the surgical instrument 8. When the surgical instrument 8 is removed, the lower sliders 22 of a lower guiding mechanism 2 have the guiding effect and facilitate the removing of the surgical instrument, and restore to the initial state without the inserting of the surgical instrument under the effect of the elastic resilience of the sealing ring 3, that is, the surgical instrument through hole 31 of the sealing ring restores to the initial diameter, and meanwhile, the upper sliders 11 and the lower sliders 22 also restore to the initial position without the inserting of the surgical instrument.

FIG. 2-3 is a side view of FIG. 2-1.

FIG. 2-4 is a schematic three-dimensional structural diagram of an upper guiding mechanism in the upper part of FIG. 2-3.

FIG. 2-5 is a schematic three-dimensional structural diagram of a lower guiding mechanism in the lower part of FIG. 2-3.

FIG. 2-6 is a schematic structural diagram of a trocar including the low-resistance general sealing apparatus according to the present invention.

FIG. 2-7 is an exploded view of FIG. 2-3.

FIG. 2-7A is a schematic structural diagram of a connection locking mechanism that connects the upper guiding mechanism and the lower guiding mechanism together fixedly through heat seal or binding using a binder.

FIG. 2-7B is a schematic structural diagram of a connection locking mechanism that connects the upper guiding mechanism and the lower guiding mechanism together fixedly through a concave-convex matching structure.

FIG. 2-8 is a schematic three-dimensional structural diagram of a trapezoidal sealing ring used in the present invention.

FIG. 2-9 is a schematic structural diagram of a cross section of the sealing ring in FIG. 2-8.

FIG. 2-10 is a schematic three-dimensional structural diagram of an quasi-trapezoidal sealing ring used in the present invention.

FIG. 2-11 is a schematic structural diagram of a cross section of the sealing ring in FIG. 2-10.

FIG. 3-1 is a schematic structural diagram of a low-resistance general sealing apparatus adopting a dynamic connection mechanism of shaft connection according to the present invention.

FIG. 3-2 is a B-B sectional view of FIG. 3-1.

In FIG. 3-2, $D_{31}$ is the diameter of a surgical instrument through hole of a sealing ring, $D_{12}$ is the position of an arc with the diameter being 12 mm, L-SH represents the length of a "soft-hard" friction area formed between a silica gel sealing ring and a surgical instrument after a 12 mm surgical instrument is inserted, and L-HH represents the length of a "hard-hard" friction area formed between the plastics of n upper guiding surface 111 and an outer metal sheath of the surgical instrument after the 12 mm surgical instrument is inserted. The difference between this embodiment and the embodiment shown in FIGS. 2-1 to 2-7 lies in that: in this embodiment, a dynamic connection mechanism 112 adopts an axial limit rotation mechanism, and a rotation shaft 1122 is disposed at the upper side of an upper guiding mechanism 1 and forms a shaft limit rotation mechanism with a shaft positioning groove 1124 on a positioning block 52 of a trocar, so as to serve as a dynamic connection mechanism 4.

FIG. 3-3 is a schematic three-dimensional structural diagram of a lower guiding mechanism in the lower part of FIG. 3-1.

FIG. 3-4 is a schematic three-dimensional structural diagram of the upper guiding mechanism in the upper part of FIG. 3-1.

FIG. 3-5 is an exploded view of FIG. 3-1.

FIG. 3-6 is a schematic structural diagram of a low-resistance general sealing apparatus adopting the dynamic connection mechanism of ball connection according to the present invention.

In FIG. 3-6, the difference from the dynamic connection mechanism adopting shaft connection shown in FIG. 3-1 to FIG. 3-5 lies in that: the rotation shaft 1122 is changed into a rotatable ball 1123, and the shaft positioning groove 1124 matched with the rotation shaft 1122 is also changed into a matched spherical positioning groove 1125, so the ball 1123 and the spherical positioning groove 1125 form a spherical limit rotation mechanism to serve as a dynamic connection mechanism 4.

FIG. 4-1 is a schematic structural diagram of a sealing apparatus adopting a connection locking mechanism of concave-convex matching according to the present invention.

FIG. 4-2 is a C-C sectional view of FIG. 4-1.

In FIG. 4-2, the difference from FIG. 2-1 to FIG. 2-7 lies in that: the fixed connection between an upper slider 11 of an upper guiding mechanism 1 and a lower slider 21 of a lower guiding mechanism 2 is locked through a connection locking mechanism 4 by means of concave-convex matching. A convex lock pin 41 is directly fabricated on the same part with the lower slider 21; and similarly, a concave lock slot 42 is also directly formed at the bottom of the upper slider 11.

FIG. 4-3 is a schematic three-dimensional structural diagram of the upper guiding mechanism in the upper part of FIG. 4-1.

FIG. 4-4 is a three-dimensional schematic structural diagram of the lower guiding mechanism in the lower part of FIG. 4-1.

FIG. 5-1 is a schematic structural diagram of a low-resistance general sealing apparatus provided with a side flapper according to the present invention.

FIG. 5-2 is a D-D sectional view of FIG. 5-1.

In FIG. 5-2, the difference from FIG. 2-1 to FIG. 2-7 lies in that: a side flapper 113 is added at the outer side of an upper slider 11 of an upper guiding mechanism 1. The objective of adding the side flapper 113, in one aspect, is improving the stiffness of the upper slider 11, and in another aspect, is increasing the support force for a bevel edge 32 of a sealing ring.

FIG. 5-3 is a schematic three-dimensional structural diagram of the upper guiding mechanism in the upper part of FIG. 5-1.

FIG. 5-4 is a schematic three-dimensional structural diagram of a lower guiding mechanism in the lower part of FIG. 5-1.

FIG. 6-1 is a schematic structural diagram of a sealing apparatus provided with a connection locking mechanism on the bevel edge of the sealing ring according to the present invention.

FIG. 6-2 is an E-E sectional view of FIG. 6-1.

In FIG. 6-2, the difference from FIG. 5-1 to FIG. 5-4 lies in that: a side flapper 113 is added on the outer side of an upper slider 11 of an upper guiding mechanism 1. The objective of adding the side flapper 113, in one aspect, is improving the stiffness of the upper slider 11, and in another aspect, is increasing the support force for a bevel edge 32 of a sealing ring. The side flapper 113 is locked fixedly with a lower slider 21 at the side face of the bevel edge 32 of the sealing ring through the connection locking mechanism 4. Here, the connection locking mechanism 4 compresses the bevel edge 32 of the sealing ring fixedly between the side flapper 113 and the lower slider 21 through a concave-convex matching structure. When the connection locking mechanism 4 locks the upper slider 11 and the lower slider 21 fixedly, the sealing ring 3 has certain compression deformation, so as to prevent gas leakage in this area that affects the sealing effect.

FIG. 6-3 is a schematic three-dimensional structural diagram of the upper guiding mechanism in the upper part of FIG. 6-1.

FIG. 6-4 is a schematic three-dimensional structural diagram of a lower guiding mechanism in the lower part of FIG. 6-1.

FIG. 7-1 is a schematic structural diagram of a 3-petal low-resistance general sealing apparatus according to the present invention.

FIG. 7-2 is an F-F sectional view of FIG. 7-1.

In FIG. 7-2, the difference from the embodiment shown in FIGS. 2-1 to 2-7 lies in: in FIG. 7-2, an upper guiding mechanism 1 is provided with 3 upper sliders 11, and a lower guiding mechanism 2 is also provided with 3 lower sliders 21, the upper sliders 11 are one to one corresponding to the lower sliders 21, thus forming a 3-petal structure. When a surgical instrument is inserted, the upper sliders 11, the lower sliders 21 and a sealing ring 3 splay outward, the gap 13 between the upper sliders and the gap 23 between the lower sliders gradually enlarge. When a surgical instrument is removed, under the effect of elastic resilience of the sealing ring 3, the upper sliders 11 and the lower sliders 21 contract centripetally, the gap 13 between the upper sliders and the gap 23 between the lower sliders gradually decrease, the upper sliders 11 and the lower sliders 21 restore to the initial position, and a surgical instrument through hole 31 of the sealing ring 3 also restores to the initial diameter.

FIG. 7-3 is a schematic three-dimensional structural diagram of the upper guiding mechanism in the upper part of FIG. 7-1.

FIG. 7-4 is a schematic three-dimensional structural diagram of the lower guiding mechanism in the lower part of FIG. 7-1.

FIG. 8-1 is a schematic structural diagram of a 2-petal low-resistance general sealing apparatus according to the present invention.

FIG. 8-2 is a J-J sectional view of FIG. 8-1.

In FIG. 8-2, the difference from the embodiment shown in FIGS. 7-1 to 7-4 lies in: in FIG. 8-2, an upper guiding mechanism 1 is provided with 2 upper sliders 11, a lower guiding mechanism 2 is also provided with 2 lower sliders 21, and the upper sliders 11 are one to one corresponding to the lower sliders 21, thus forming a 2-petal structure.

FIG. 8-3 is a schematic three-dimensional structural diagram of the upper guiding mechanism in the upper part of FIG. 8-1.

FIG. 8-4 is a schematic three-dimensional structural diagram of the lower guiding mechanism in the lower part of FIG. 8-1.

FIG. 9-1 is a schematic structural diagram of a 2-petal low-resistance general sealing apparatus according to the present invention.

FIG. 9-2 is a K-K sectional view of FIG. 9-1.

In FIG. 9-2, the difference from the embodiment shown in FIGS. 8-1 to 8-4 lies in that: in the embodiment shown in FIGS. 8-1 to 8-4, the cross section of a sealing ring 3 is trapezoidal. In this embodiment, the cross section of a sealing ring 3 is V-shaped. In the embodiment shown in FIGS. 8-1 to 8-4, the upper sliders 11 and lower sliders 21 are locked fixedly at the bottom 34 of the trapezoidal sealing ring through the connection locking mechanism 4 of a concave-convex matching structure, and the sealing ring 3 is located between the upper sliders 11 and the lower sliders 21. However, in this embodiment, upper sliders 11 and lower sliders 21 are locked fixedly on a bevel edge 32 of the V-shaped sealing ring through a connection locking mechanism 4 of the concave-convex matching structure, and the sealing ring 3 is located between the upper sliders 11 and the lower sliders 21. However, in both of the two embodiments, a smooth transition is formed between the upper sliders 11 and the lower sliders 21, with a layer of thin sealing ring 3 being sandwiched.

FIG. 9-3 is a schematic three-dimensional structural diagram of an upper guiding mechanism in the upper part of FIG. 9-1.

FIG. 9-4 is a schematic three-dimensional structural diagram of a lower guiding mechanism in the lower part of FIG. 9-1.

FIG. 10-1 is a schematic structural diagram of a 4-segment low-resistance general sealing apparatus having an approximately H-shaped sealing ring according to the present invention.

FIG. 10-2 is an M-M sectional view of FIG. 9-1.

In FIG. 10-2, the difference from the embodiment shown in FIGS. 2-1 to 2-7 lies in that: in the embodiment shown in FIGS. 2-1 to 2-7, the cross section of the sealing ring 3 is trapezoidal, but in this embodiment, the cross section of the sealing ring 3 is approximately H-shaped.

The characteristic of an H-shaped sealing ring or approximately H-shaped sealing ring lies in that: the upper part is a trapezoidal sealing ring, and the lower part has an inverted funnel-shaped sealing ring that is connected to the bottom of the trapezoidal sealing ring. A bevel edge of the inverted funnel-shaped sealing ring may increase the elastic resilience after the deformation of the silica gel sealing ring, so as to increase the capability for upper sliders 11 and lower sliders 21 to restore to the initial position.

Figures 2, 3:
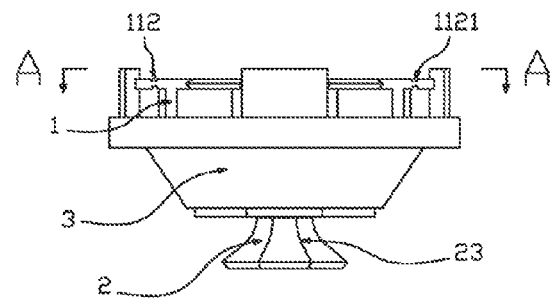
Figures 2, 3, 4:
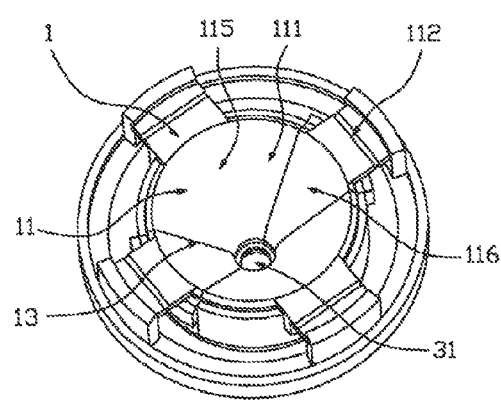
Figures 2, 3, 4, 5:
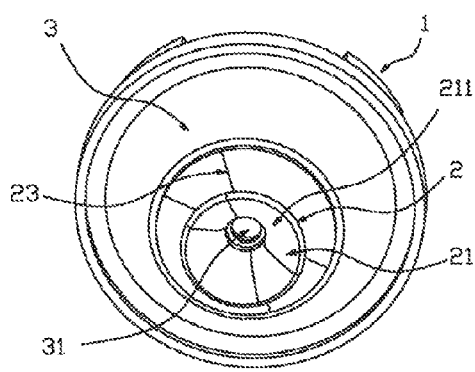
Figures 2, 3, 4, 5, 6:
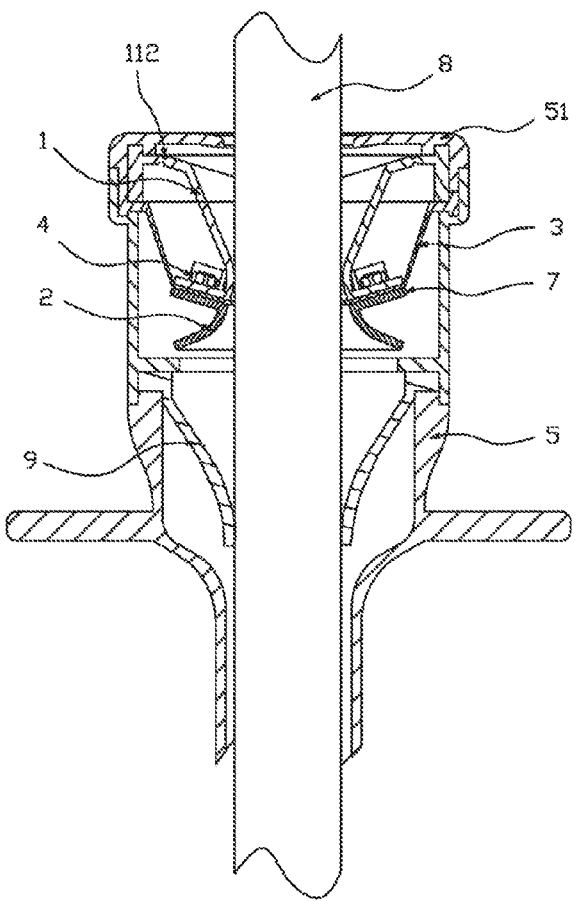
Figures 2, 3, 4, 5, 6, 7, 7A, 7B:
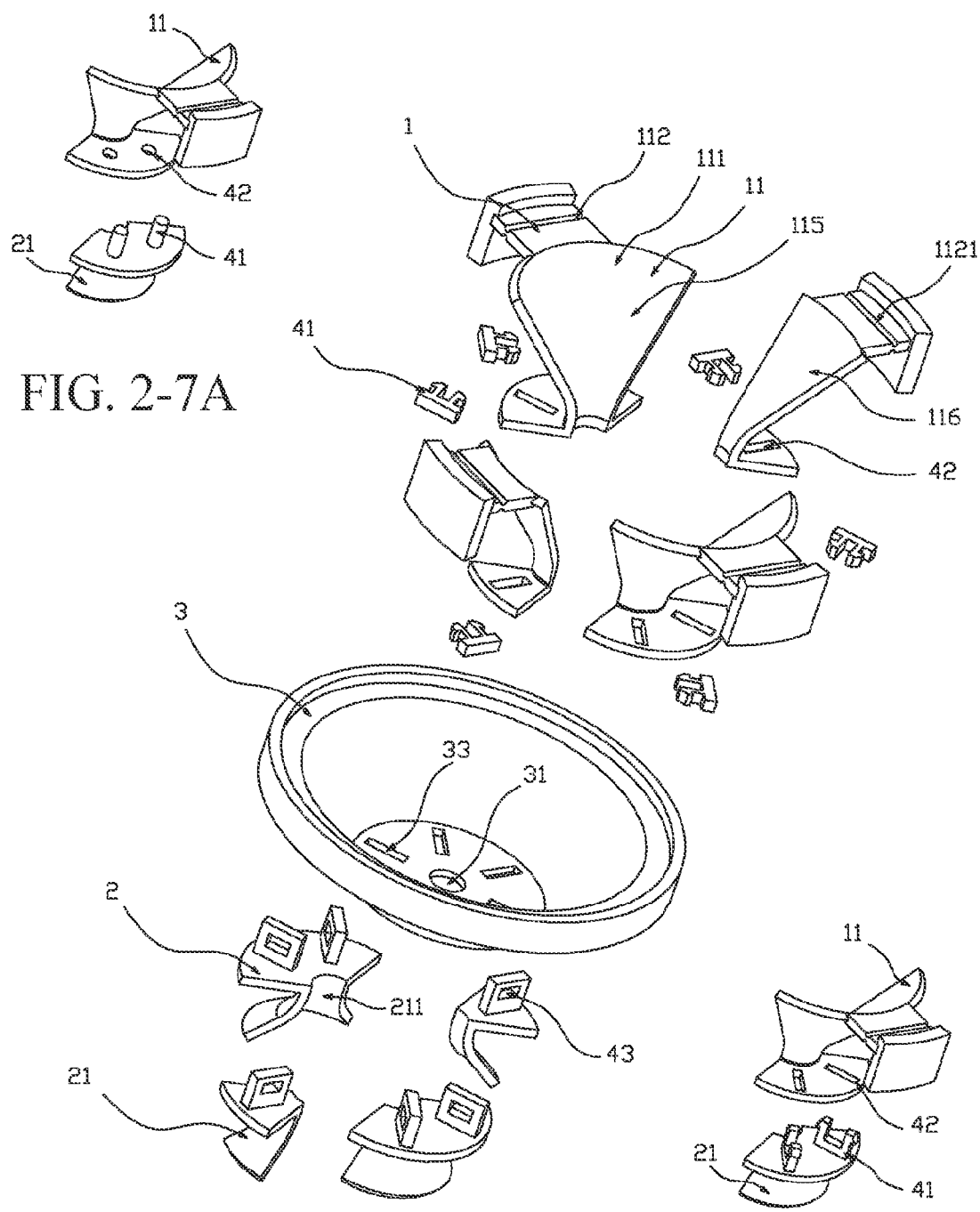
Figures 2, 3, 4, 5, 6, 7, 8:
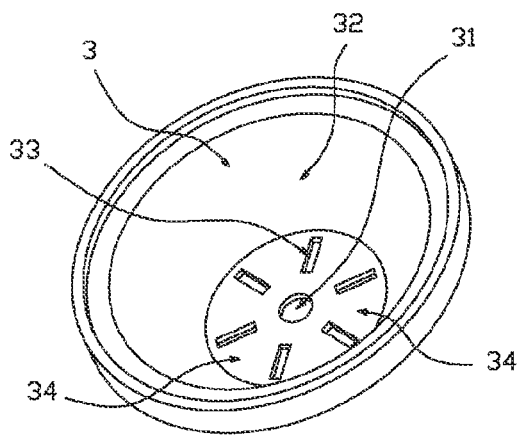
Figures 2, 3, 4, 5, 6, 7, 8, 9:
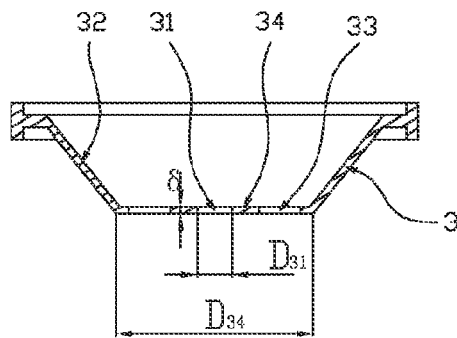
Figures 2, 3, 4, 5, 6, 7, 8, 9, 10:
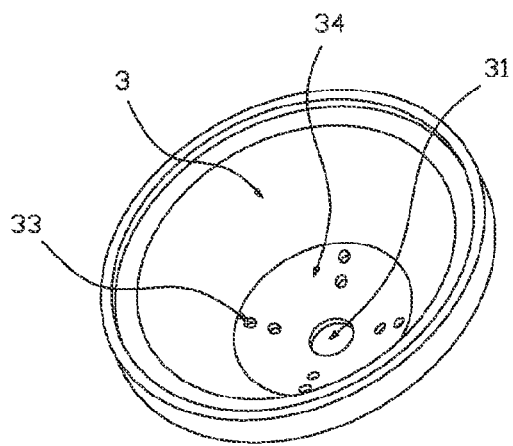
Figures 1, 4:
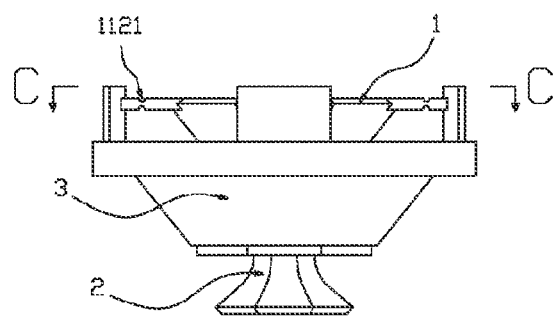
Figures 2, 4:
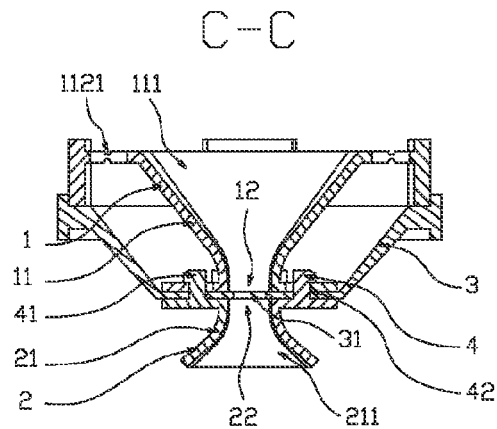
Figures 3, 4:
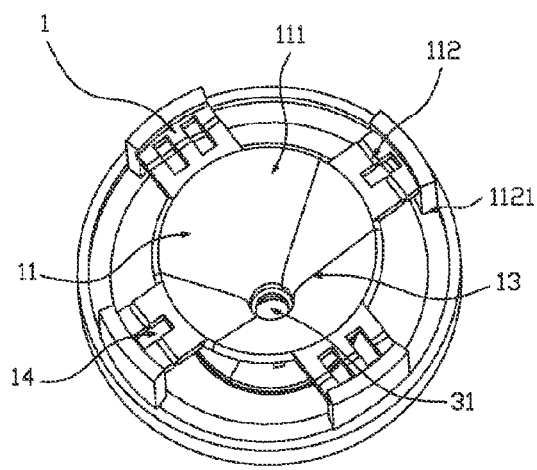
Figure 4:
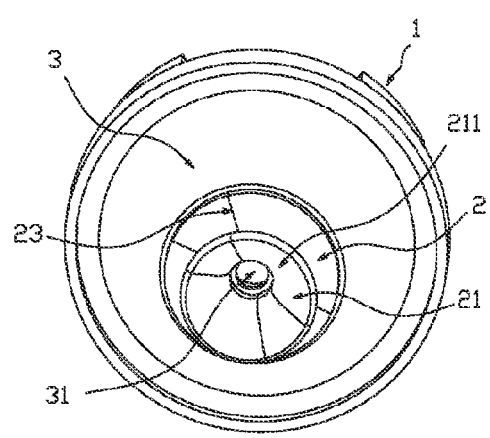
Figures 1, 5:
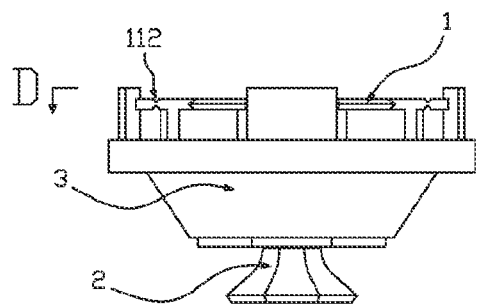
Figures 2, 5:
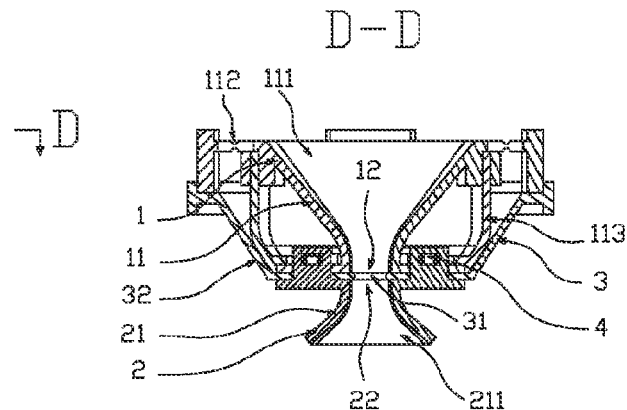
Figures 3, 5:
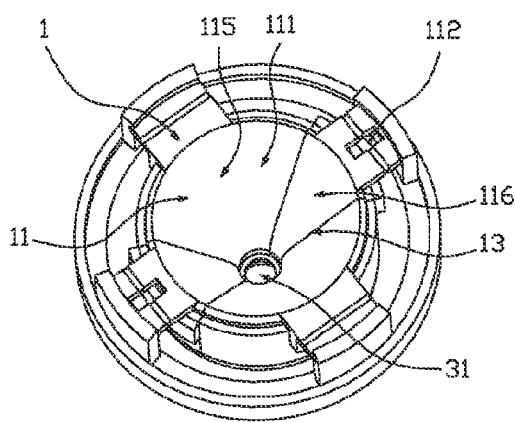
Figures 4, 5:
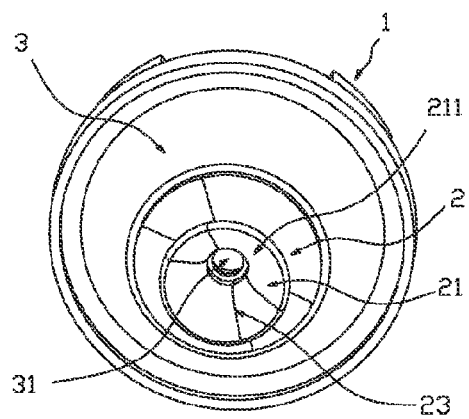
Figures 1, 6:
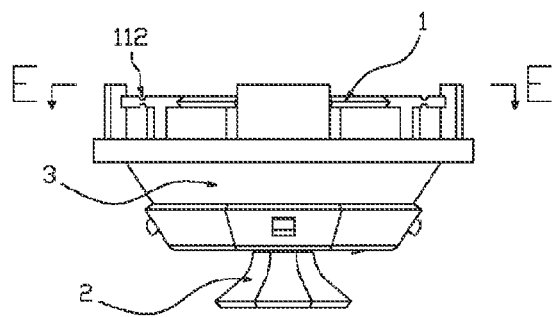
Figures 2, 6:
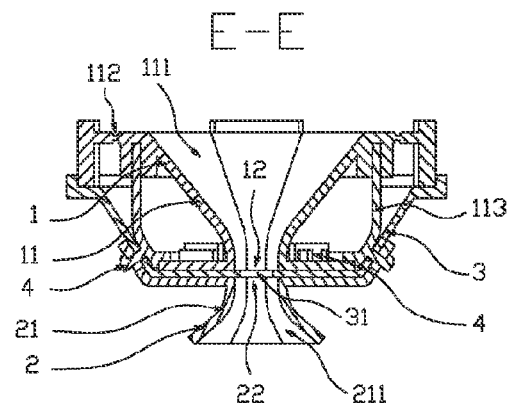
Figures 3, 6:
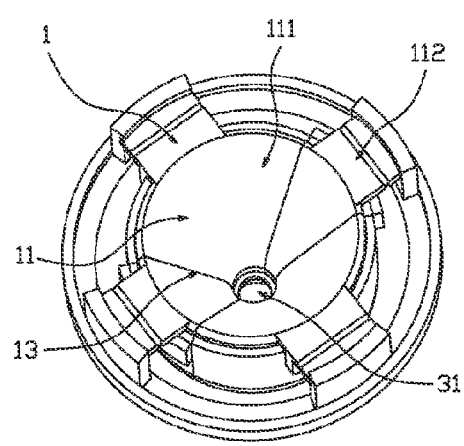
Figures 4, 6:
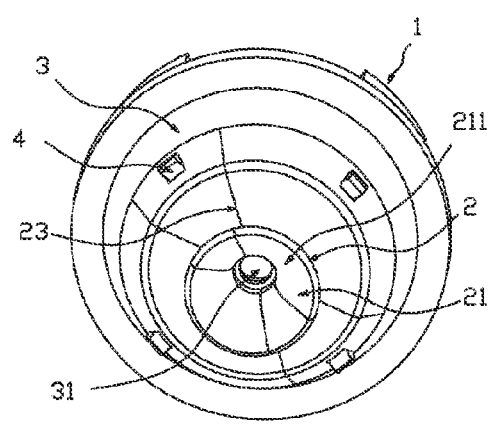
Figures 1, 7:
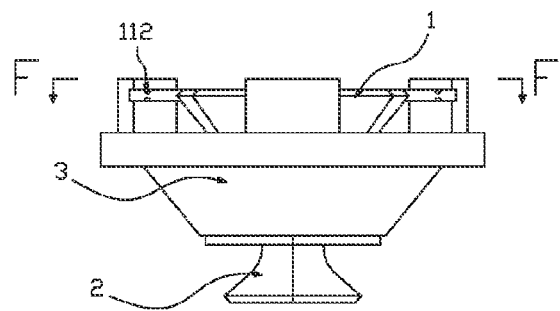
Figures 2, 7:
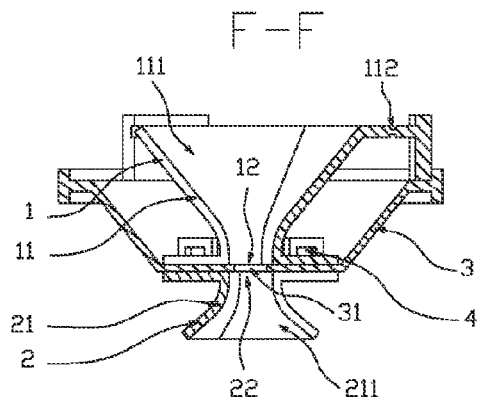
Figures 3, 7:
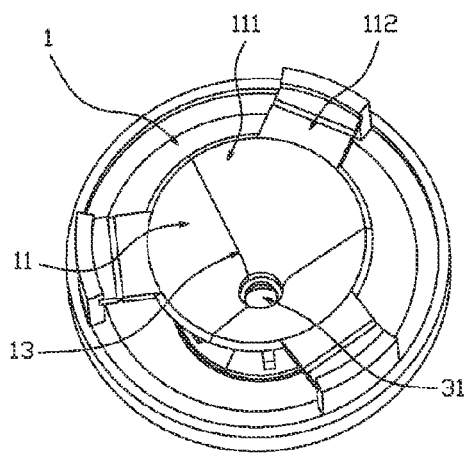
Figures 4, 7:
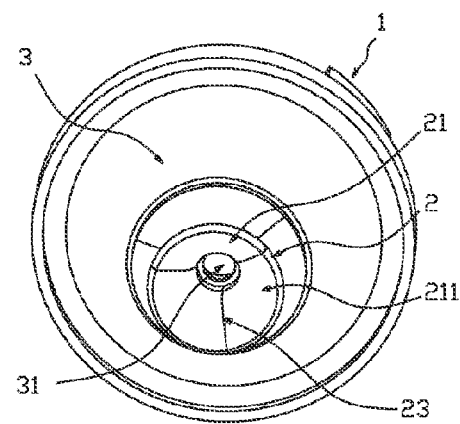
Figures 1, 9:
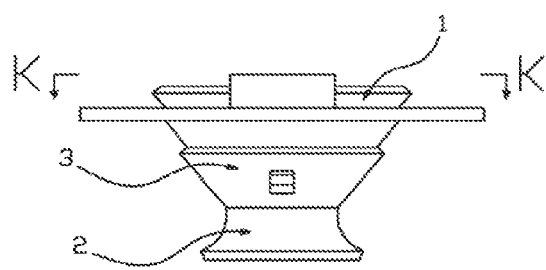
Figures 2, 9:
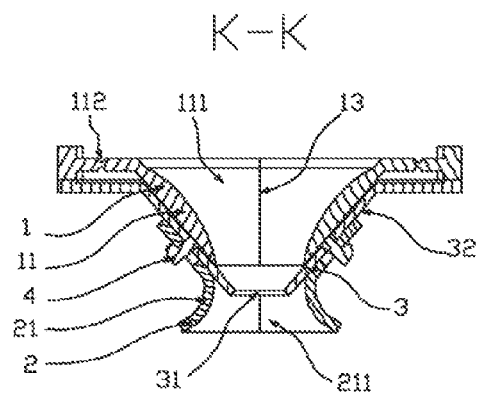
Figures 3, 9:
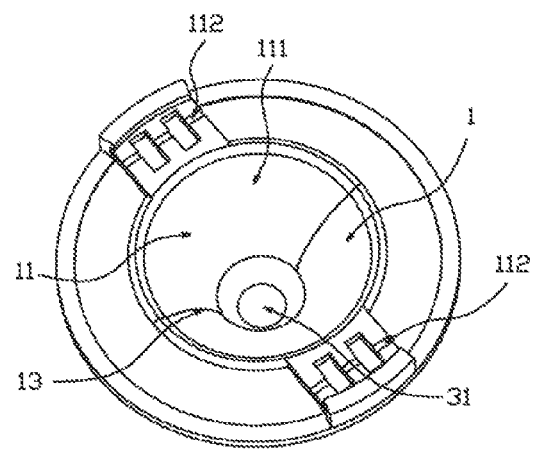
Figures 4, 9:
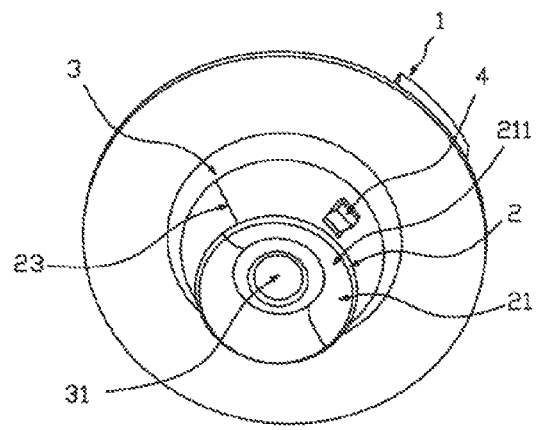
Figures 1, 10:
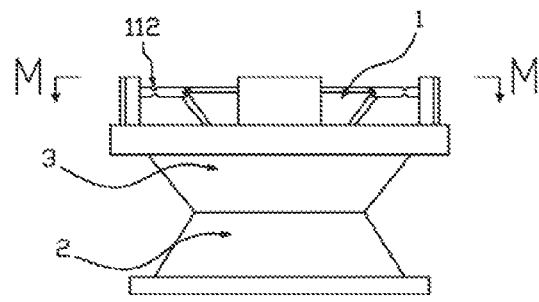
Figures 2, 10:
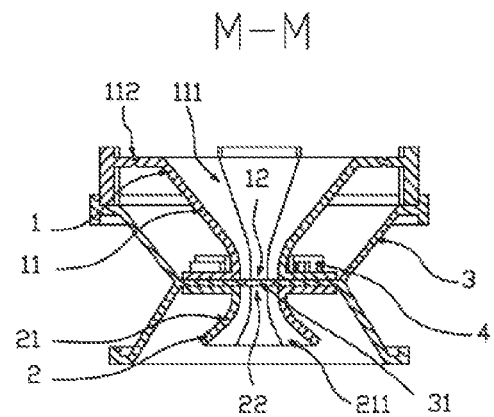
Figures 3, 10:
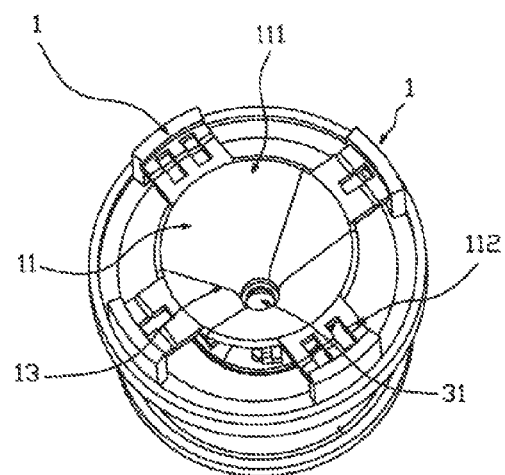
Figures 4, 10:
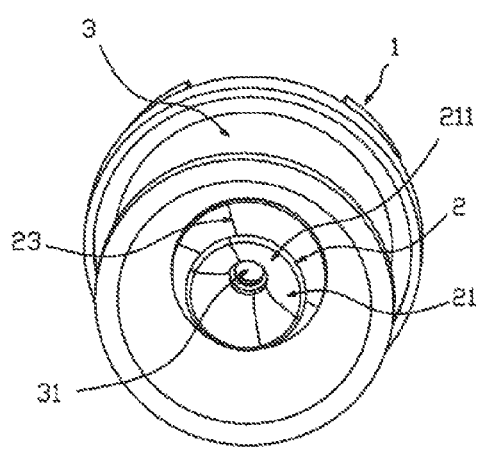
Figures 1, 11:
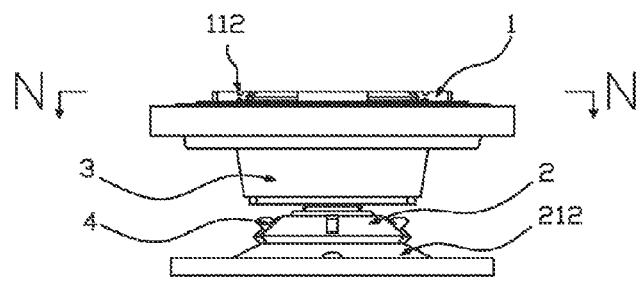
Figures 2, 11:
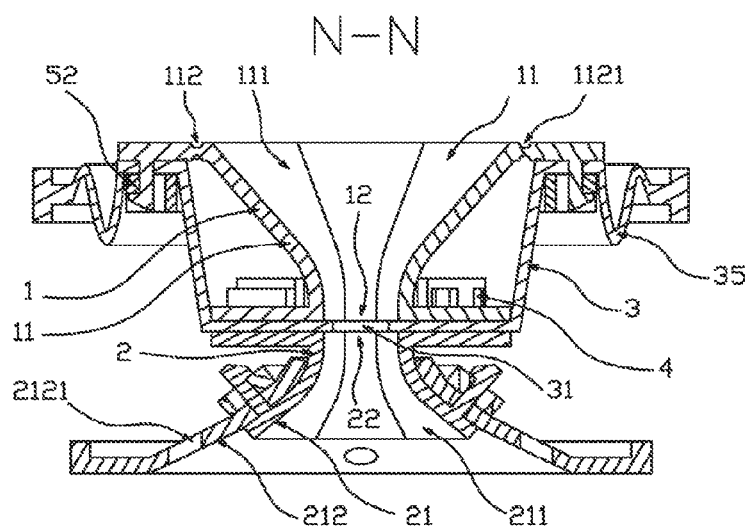
Figures 3, 11:
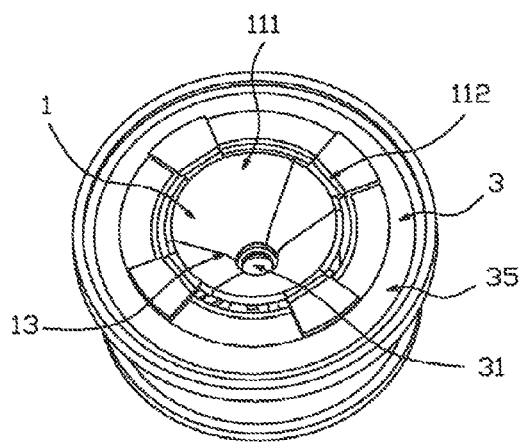
Figures 4, 11:
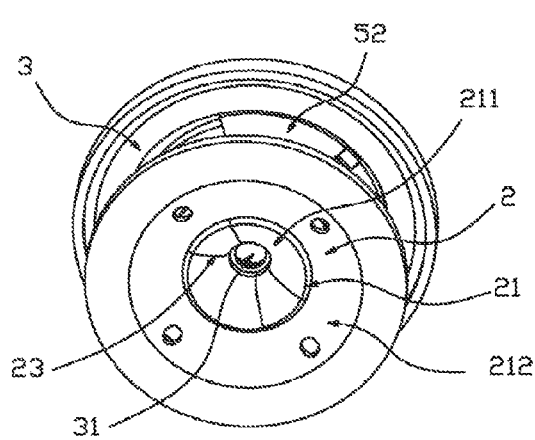

FIG. 10-3 is a schematic three-dimensional structural diagram of an upper guiding mechanism in the upper part FIG. 10-1.

FIG. 10-4 is a schematic three-dimensional structural diagram of a lower guiding mechanism in the lower part of FIG. 10-1.

Figures 2, 3, 4, 5, 6, 7, 8, 9, 10, 11:
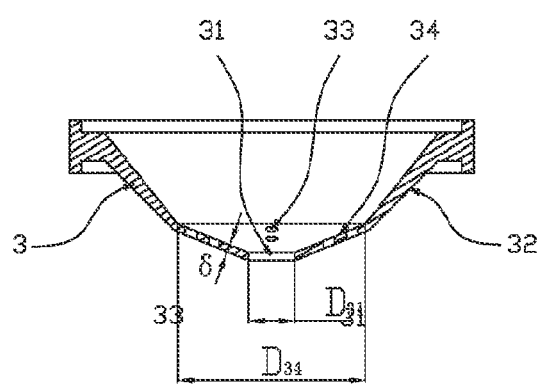

FIG. 11-1 is a schematic structural diagram of a 4-segment low-resistance general sealing apparatus provided with a buffering ring and a traction plate according to the present invention.

FIG. 11-2 is an N—N sectional view of FIG. 11-1.

In FIG. 11-2, the lower part of the lower slider 21 of the lower guiding mechanism is provided with a traction plate 212, and the traction plate 212 is made of an elastic medical macromolecular material selected from flexible medical materials such as medical silica gel, medical rubber, medical polyurethane and medical latex. The traction plate 212 is fixed at the lower part of the lower slider 21 through concave-convex matching.

The traction plate 212 has a traction effort on the lower sliders 21 when a surgical instrument 8 is removed, the elastic resilience is also conducive to the restoration of the lower sliders 21 when the surgical instrument 8 is completely removed; and meanwhile, the traction plate 212 is soft and does not affect the motion of splaying outward of the lower sliders 21 when the surgical instrument 8 is inserted.

In FIG. 11-2, a ripple buffering ring 35 is further disposed at the edge of a sealing ring 3, the buffering ring 35 is used to perform buffering and sealing when an upper guiding mechanism 1 and a lower guiding mechanism 2 are in horizontal motion. A dynamic connection mechanism 112 of an upper slider 11 of the upper guiding mechanism 1 is fixed together with a positioning block 52 through a matching locking device. In this embodiment, upper guiding blocks 11, lower guiding blocks 21 and the sealing ring 3 can splay outward cooperatively when the surgical instrument 8 is inserted. When the surgical instrument 8 is removed, under the effect of elastic resilience of the sealing ring 3, the upper guiding blocks 11, the lower guiding blocks 21 and the sealing ring 3 can centripetally contract to restore to the initial position. Additionally, the dynamic connection mechanism 112 is fixed with the positioning block 52, where the upper side of the silica gel sealing ring is compressed fixedly between the dynamic connection mechanism 112 and the positioning block 52. The upper edge of the sealing ring 3 is provided with the buffering ring 35, so the upper guiding mechanism 1, the lower guiding mechanism 2 and the surgical instrument through hole 31 of the sealing ring 3 can perform 2-dimensional translational motion along the horizontal direction, thereby satisfying different motion requirements of surgical operations.

FIG. 11-3 is a schematic three-dimensional structural diagram of the upper guiding mechanism in the upper part of FIG. 11-1.

FIG. 11-4 is a schematic three-dimensional structural diagram of the lower guiding mechanism in the lower part of FIG. 11-1.

FIG. 12-1 is a schematic structural diagram of a trocar adopting a groove type dynamic connection mechanism according to the present invention.

FIG. 12-2 is a schematic structural diagram a sheath of the trocar of FIG. 12-1.

FIG. 12-3 is an operation principle diagram of the trocar after a surgical instrument is inserted in FIG. 12-1.

FIG. 13-1 is a schematic structural diagram of a trocar adopting a rotation shaft type connection mechanism according to the present invention.

FIG. 13-2 is an operation principle diagram of the trocar after a surgical instrument is inserted in FIG. 13-1.

In the foregoing accompanying drawings:

1 is an upper guiding mechanism, 2 is a lower guiding mechanism, 3 is a sealing ring, 4 is a connection locking mechanism, 5 is a trocar of the present invention, 6 is a trocar rod, 7 is a sealing apparatus of the present invention, 8 is a surgical instrument, and 9 is a check valve or an axial sealing apparatus.

11 is an upper slider of the upper guiding mechanism, 12 is a through hole at the bottom of the upper guiding mechanism, 13 is gap between upper sliders, 14 is a through hole disposed for degrading the intensity; 111 is a guiding surface on the upper slider, 112 is a dynamic connection mechanism on the upper slider, 113 is a side flapper of the upper slider; 115 is a main guiding slider, and 116 is an auxiliary guiding slider.

1121 is a dynamic connection mechanism of a groove or an elastic weak-intensity area style, 1122 is a dynamic connection mechanism of a rotation shaft connection style, 1123 is a dynamic connection mechanism of a rotation ball connection style, 1124 is a shaft limit slot, and 1125 is a ball limit slot.

21 is a lower slider of a lower guiding mechanism, 22 is a through hole on the upper side of the lower guiding mechanism, 23 is the gap between lower sliders; 211 is a guiding surface of the lower slider, 212 is a traction plate; and 2121 is a through hole on the traction plate.

31 is a surgical instrument through hole of the sealing ring, 32 is a bevel edge of the sealing ring, 33 is a through hole on the sealing ring enabling a connection locking mechanism to pass through, 34 is the bottom of the trapezoidal sealing ring, and 35 is a buffering ring.

41 is a lock pin of the connection locking mechanism, 42 is a lock slot of the connection locking mechanism, and 43 is a positioning groove of the connection locking mechanism.

51 is a housing of a trocar and 52 is a positioning block.

$D_{12}$ is the position of an arc with the diameter being 12 mm, $D_{31}$ is the diameter of the surgical instrument through hole of the sealing ring, and $D_{34}$ is the diameter of the bottom of the trapezoidal sealing ring.

L-SH is the length of a "soft-hard" friction area formed between the silica gel sealing ring and a surgical instrument after a 12 mm surgical instrument is inserted, and L-HH is the length of a "hard-hard" friction area formed between the plastics of upper guiding surfaces and an outer metal sheath of the surgical instrument after a 12 mm surgical instrument is inserted.

β is an angle between the upper guiding surface of the upper guiding mechanism and a central shaft of a funnel-shaped structure of the upper guiding mechanism.

DETAILED DESCRIPTION

Embodiment 1: A 4-segmentine low-resistance general sealing apparatus according to the present invention Referring to FIG. 2-1 to FIG. 2-11, specific part drawings designed according to technical solutions of the present invention are shown.

Upper sliders 11, lower sliders 21 and a connection locking mechanism 4 are made of medical macromolecular materials including, but not limited to, medical plastics such as medical PP, medical PE, medical PU, medical PA and medical PC. An ultra smooth material coating may be arranged on a guiding surface 111 of the upper slider and a guiding surface 211 of the lower slider to reduce frictional resistance when a surgical instrument moves.

A sealing ring 3 is made of a medical elastic material including, but not limited to, flexible medical materials such as medical silica gel, medical rubber, medical polyurethane, and medical latex.

In assembling, the sealing ring 3 is placed between an upper guiding mechanism 1 and a lower guiding mechanism 2, and the upper sliders 11 and the lower sliders 21 are connected together fixedly through the connection locking mechanism 4. The edge of a surgical instrument through hole 31 of the sealing ring is fixed between the upper sliders 11 and the lower sliders 21, so that a smooth transition is formed between the upper sliders 11 and the lower sliders 21, with a layer of thin sealing ring 3 being sandwiched.

The sealing ring 3 is compressed between the upper guiding mechanism 1 and the lower guiding mechanism 2, and the smooth transition between the upper guiding mechanism 1 and the lower guiding mechanism 2 minimizes the contact area between the sealing ring 3 and the surgical instrument. The sealing apparatus of the present invention greatly shortens the length L-SH of a "soft-hard" friction area formed between the silica gel sealing ring 3 and an outer metal sheath of a surgical instrument 8 after a 12 mm surgical instrument is inserted, compared with the length L-SH of a "soft-hard" friction area formed between a conventional funnel-shaped general silica gel sealing ring and a surgical instrument, thereby reducing the frictional resistance when the surgical instrument moves.

After the surgical instrument is inserted, the length L-SH of the "soft-hard" friction area of the sealing apparatus of the present invention is comparable to the thickness δ of the bottom of the sealing ring 3, unlike the great increase of the length L-SH of the funnel-shaped general silica gel sealing ring in the "soft-hard" friction area after the surgical instrument is inserted in the prior art. The sealing apparatus of the present invention only increases the length L-HH of the "hard-hard" friction area and replaces the length L-SH of the "soft-hard" friction area with the length L-HH of the "hard-hard" friction area, thereby fundamentally reducing the motion resistance when the surgical instrument is in reciprocal motion.

The sealing apparatus of the present invention not only has a guiding function when an instrument is inserted or removed, being applicable to insertion and removal of all forms of surgical instruments; but also maximally transforms the "soft-hard" friction area between the sealing ring 3 and the surgical instrument into the "hard-hard" friction area between upper and lower guiding surfaces and the instrument, thereby greatly reducing the motion resistance of the surgical instrument in the sealing apparatus and the trocar. Meanwhile, the sealing apparatus and the trocar of the present invention are applicable to instruments with diameters 5 mm and 12 mm to implement the generality, with excellent sealing effect and low motion resistance.

Additionally, the lower guiding mechanism 1 of the sealing apparatus of the present invention not only has a guiding function, but also has an effect of preventing turnover of the sealing ring when the surgical instrument is withdrawn outward. The turnover of the sealing ring greatly increases the resistance of the withdrawing of the surgical instrument, so the sealing apparatus of the present invention avoids the turnover phenomenon.

By means of the sealing apparatus of the present invention, surgical instruments with the diameters between 5 mm and 12 mm can be inserted while maintaining excellent dynamic sealing performance. The sealing apparatus and the trocar of the present invention can further implement free changing of the surgical instruments with diameters between 5 mm and 15 mm while maintaining low motion resistance.

In this embodiment, the upper guiding mechanism 1 is provided with 4 upper sliders 11, the lower guiding mechanism 2 is also provided with 4 lower sliders 21, and the upper sliders 11 are one to one corresponding to the lower sliders 21, thereby forming a 4-segment structure.

When the surgical instrument 8 is inserted, the upper sliders 11, the lower sliders 21 and the sealing ring 3 splay outward, and 4 gaps 13 gradually enlarge. The sealing ring 3 between the upper sliders 11 and the lower sliders 21 also deforms elastically due to the inserting of the surgical instrument.

When the surgical instrument 8 is removed, under the effect of elastic resilience of the sealing ring 3, the upper sliders 11 and the lower sliders 21 contract centripetally to restore to the initial position. Meanwhile, the surgical instrument through hole 31 of the sealing ring 3 also restores to the initial diameter.

Here, the connection locking mechanism 4 is formed by a lock pin 41, a lock slot 42, and a positioning groove 43; a convex lock slot 42 on the lower slider 21 passes through a through hole 33 on the sealing ring to insert into a positioning groove 43 of the upper slider 11, the lock pin 41 passes through the lock slot 42 to connect the upper slider 11 and the lower slider 21 together fixedly, and the sealing ring 3 is placed between the upper slider 11 and the lower slider 21. A smooth transition is formed between the upper slider 11 and the corresponding lower slider 21; and the diameter of the surgical instrument through hole 31 of the sealing ring is smaller than that of a lower through hole 12 of the upper guiding mechanism 1 and an upper through hole 22 of the lower guiding mechanism.

The sealing ring 3 is compressed fixedly between the upper sliders 11 and the lower sliders 21 through the connection locking mechanism 4 of a concave-convex matching structure. When the connection locking mechanism 4 locks the upper sliders 11 and the lower sliders 21 fixedly, the sealing ring 3 has certain compression deformation to prevent gas leakage in this area that affects the sealing effect.

In this embodiment, a dynamic connection mechanism 112 of the upper guiding mechanism 1 is implemented through an elastic weak-intensity area formed by a groove 1121 on the upper side of the guiding surface 111. The groove 1121 forms the elastic weak-intensity area, the intensity of the upper slider 11 in the area is low and the area is easy to deform, so when the surgical instrument 8 is inserted, the groove deforms and drives the upper sliders 11, the lower sliders 22 and the sealing ring 3 to splay outward, so as to facilitate the inserting of the surgical instrument. When the surgical instrument is removed, the lower sliders 22 of the lower guiding mechanism 2 have the guiding effect, thereby facilitating the removing of the surgical instrument 8, and under the effect of the elastic resilience of the sealing ring 3, the sealing ring 3 restores to a state without the inserting of the instrument, that is, the surgical instrument through hole 31 of the sealing ring restores to the initial diameter.

Referring to FIG. 2-7A, this embodiment shows a basic structure of the connection locking mechanism 4 that connects the upper guiding mechanism 1 and the lower guiding mechanism 2 together fixedly through heat seal or binding using a binder. The convex lock pin 41 of the lower slider passes through the bottom 34 of the silica gel sealing ring 3 to insert into a groove 42 of the bottom of an upper guiding block to form concave-convex matching, and in this place, an ultrasonic wave heat seal technique may be adopted to heat seal the upper sliders 11 and the lower sliders 21 together fixedly. Another method is to use a chemical binder in the concave-convex matching area to bind the upper sliders 11 and the lower sliders 21 together fixedly.

Referring to FIG. 2-7B, this embodiment shows a structure of a connection locking mechanism 4 that connects the upper guiding mechanism 1 and the lower guiding mechanism 2 together fixedly through a concave-convex matching structure. The lock pin 41 is directly fabricated on the lower slider 21, and correspondingly, a lock slot 42 is disposed at the corresponding position of the upper slider 11. After passing through the bottom 34 of the silicone gel sealing ring 3, the lock pin 41 is inserted into the groove 42 at the bottom of the upper guiding block to form concave-convex matching, thereby connecting the upper sliders 11 and the lower sliders 21 together fixedly.

Embodiment 2: A sealing apparatus adopting a shaft connection style dynamic connection mechanism according to the present invention Referring to FIG. 3-1 to FIG. 3-5, the technical principles of this embodiment are similar to those of Embodiment 1, and the difference only lies in that: in Embodiment 1, the dynamic connection mechanism 112 adopts a weak-intensity area formed by a groove, while in this embodiment, the dynamic connection mechanism 112 adopts a dynamic connection manner of a rotation shaft, and the rotation shaft 1122 and a shaft positioning groove 1124 disposed on a positioning block 52 of a trocar form dynamic connection between the shaft positioning groove and the rotation shaft. There are multiple specific connection manners between the rotation shaft and the shaft positioning groove, which can be designed by professional engineers according to specific situations.

FIG. 3-6 shows a spherical limit rotation mechanism as the dynamic connection mechanism 112. In this embodiment, the rotation shaft 1122 is changed into a rotatable ball 1123, and the shaft positioning groove 1124 matched with the rotation shaft 1122 is also changed into a spherical positioning groove 1125 matched with the rotatable ball 1123. The ball 1123 and the spherical positioning groove 1125 form a spherical limit rotation mechanism as a dynamic connection mechanism 4.

Embodiment 3: A sealing apparatus adopting a concave-convex matching connection locking mechanism according to the present invention Referring to FIG. 4-1 to FIG. 4-4, the technical principles of this embodiment are similar to those in Embodiment 1, and the different only lies in that: the connection locking mechanism 4 of the present invention is formed by a lock pin 41 on a lower slider and a lock slot 42 on an upper slider, and the lock pin 41 is inserted upward in the lock slot 42 on the upper slider, thereby compressing a sealing ring 3 between the upper slider 11 and the lower slider 21, and forming a smooth transition between the upper and lower sliders. In the connection locking mechanism 4 formed by the concave-convex matching structure formed by the lock pin 41 and the lock slot 42, the lock pin 41 and the lower slider 21 may be integrated as a whole through injection molding, and similarly, the lock slot 42 may also be directly formed on the upper slider 11 through injection molding, thereby facilitating the fabrication.

Embodiment 4: A sealing apparatus provided with a side flapper according to the present invention Referring to FIG. 5-1 to FIG. 5-3, the technical principles of this embodiment are similar to those in Embodiment 1, and the difference of this embodiment from Embodiment 1 lies in that: the outer side of an upper slider 11 of an upper guiding mechanism 1 is added with a side flapper 113. The objective of adding the side flapper 113, in one aspect, is improving the stiffness of the upper slider 11 and preventing excessive deformation of the upper slider 11 when a surgical instrument is inserted; and in the other aspect, is increasing the support force of a bevel edge 32 of a sealing ring.

Embodiment 5: A sealing apparatus adopting a sealing ring having a bevel edge provided with a connection locking mechanism according to the present invention Referring to FIG. 6-1 to FIG. 6-4, this embodiment and Embodiment 4 are basically the same and the difference lies in: the outer side of the upper slider 11 of the upper guiding mechanism 1 is added with a side flapper 113. The objective of adding the side flapper 113, in one aspect, is improving the stiffness of the upper slider 11, and in the other aspect, is increasing the support force of the bevel edge 32 of the sealing ring. The side flapper 113 is locked fixedly with the lower slider 21 on the side face of the bevel edge 32 of the sealing ring through the connection locking mechanism 4. Here, the connection locking mechanism 4 compresses the bevel edge 32 of the sealing ring between the side flapper 113 and the lower slider 21 fixedly through the concave-convex matching structure. When the connection locking mechanism 4 locks the upper slider 11 and the lower slider 21 fixedly, the sealing ring 3 has certain compression deformation, so as to prevent gas leakage in this area that affects the sealing effect.

Embodiment 6: A 3-petal sealing apparatus according to the present invention

Referring to FIGS. 7-1 to 7-4, this embodiment and Embodiment 1 are basically the same and the difference lies in that: in this embodiment, an upper guiding mechanism 1 is provided with 3 upper sliders 11, a lower guiding mechanism 2 is also provided with 3 lower sliders 21, and the upper sliders 11 are one to one corresponding to the lower sliders 21, thereby forming a 3-petal structure.

When a surgical instrument 8 is inserted, the upper sliders 11, the lower sliders 21 and a sealing ring 3 splay outward, 3 gaps 13 gradually enlarge, and the sealing ring 3 can be seen in the gaps.

When the surgical instrument 8 is removed, under the effect of elastic resilience of the sealing ring 3, the upper sliders 11 and the lower sliders 21 contract centripetally, the gaps 13 gradually decrease to restore to the initial position, and meanwhile, a surgical instrument through hole 31 of the sealing ring 3 also restores to the initial diameter.

Embodiment 7: A 2-petal sealing apparatus according to the present invention

Referring to FIG. 8-1 to FIG. 8-4, the difference of this embodiment from Embodiment 6 lies in that: in this embodiment, an upper guiding mechanism 1 is provided with 2 upper sliders 11, a lower guiding mechanism 2 is also provided with 2 lower sliders 21, and the upper sliders 11 are one to one corresponding to the lower sliders 21, thereby forming a 2-petal structure.

Embodiment 8: A sealing apparatus adopting a 2-petal V-shaped sealing ring according to the present invention Referring to FIG. 9-1 to FIG. 9-4, the difference of this embodiment from Embodiment 7 lies in that: the cross section of the sealing ring 3 used in Embodiment 1 to Embodiment 7 is trapezoidal, while in this embodiment, the cross section of a sealing ring 3 is V-shaped.

In Embodiment 1 to Embodiment 7, the upper sliders 11 and the lower sliders 21 are locked at the bottom of the trapezoidal sealing ring 3 fixedly through the connection locking mechanism 4 of the concave-convex matching structure, and the sealing ring 3 is between the upper sliders 11 and the lower sliders 21. In this embodiment, upper sliders 11 and the lower sliders 21 are locked on a bevel edge 32 of the V-shaped sealing ring 3 fixedly through a connection locking mechanism 4 of the concave-convex matching structure, and the sealing ring 3 is between the upper sliders 11 and the lower sliders 21. However, in the two embodiments, a smooth transition is formed between the upper sliders 11 and the lower sliders 21, with a layer of thin sealing ring 3 being sandwiched.

Embodiment 9: A 4-segment sealing apparatus adopting an H-shaped sealing ring according to the present invention Referring to FIG. 10-1 to FIG. 10-4, the difference of this embodiment lies in that: the cross section of the sealing ring 3 of the embodiment shown in Embodiment 1 is trapezoidal, while in this embodiment, the cross section of the sealing ring 3 is approximately H-shaped. The characteristic of the H-shaped sealing ring or the approximately H-shaped sealing ring lies in that its upper part is a trapezoidal sealing ring, and its lower part has an inverted funnel-shaped sealing ring connected to the bottom of the trapezoidal sealing ring. The bevel edge of the inverted funnel-shaped sealing ring may increase the elastic resilience after the silica gel sealing ring deforms and increase the capability for the upper sliders 11 and the lower sliders 21 to restore to the initial position.

Embodiment 10: A 4-segment sealing apparatus adopting a sealing ring, with a ripple buffering structure, and a traction plate according to the present invention Referring to FIGS. 11-1 to 11-4, the difference of this embodiment lies in that: the sealing apparatus of the present invention is provided with a buffering ring 35, a traction plate 212 and a positioning block 52. The traction plate 212 is further provided with a gas through hole 2121.

In this embodiment, the lower side of a lower slider 21 of a lower guiding mechanism is provided with the traction plate 212, and the traction plate 212 is made of an elastic medical macromolecular material selected from flexible medical materials such as medical silica gel, medical rubber, medical polyurethane and medical latex. The traction plate 212 is fixed to the lower part of the lower slider 21 through concave-convex matching.

The traction plate 212 has a traction effort on the lower sliders 21 when the surgical instrument 8 is removed, the elastic resilience is also conducive to the reduction of the lower sliders 21 after the surgical instrument 8 is completely removed; and meanwhile, the traction plate 212 is soft and does not affect the motion of splaying outward of the lower sliders 21 when the surgical instrument 8 is inserted.

In this embodiment, the edge of the sealing ring 3 is further provided with a ripple buffering ring 35, the buffering ring 35 is used to perform buffering and sealing when an upper guiding mechanism 1 and the lower guiding mechanism 2 perform horizontal motion. A dynamic connection mechanism 112 of an upper slider 11 of the upper guiding mechanism 1 is fixed together with the positioning block 52 through a matching locking apparatus. In this embodiment, upper guiding blocks 11, lower guiding blocks 21 and the sealing ring 3 can splay outward collaboratively when the surgical instrument 8 is inserted. When the surgical instrument 8 is removed, under the effect of the elastic resilience of the sealing ring 3, the upper guiding blocks 11, the lower guiding blocks 21 and the sealing ring 3 can contract centripetally to restore to the initial position. Additionally, the dynamic connection mechanism 112 and the positioning block 52 are fixed together, where the upper side of the silica gel sealing ring is compressed fixedly between the dynamic connection mechanism 112 and the positioning block 52. The upper edge of the sealing ring 3 is provided with the buffering ring 35, so the upper guiding mechanism 1, the lower guiding mechanism 2 and the surgical instrument through hole 31 of the sealing ring 3 can perform 2-dimensional translational motion together along the horizontal direction, thereby satisfying different motion requirements of surgical operations.

Embodiment 11: A trocar adopting a groove type dynamic connection mechanism according to the present invention Referring to FIG. 12-1 to FIG. 12-3, in this embodiment, the radial sealing adopts a low-resistance general sealing apparatus of a groove type dynamic connection mechanism of the present invention, while the axial sealing, namely, a check valve 9 adopts a silicon gel straight sealing ring.

A groove 1121 forms an elastic weak-intensity area, the intensity in this area is low and it is easy to deform elastically.

When a surgical instrument 8 is inserted, the groove 1121 deforms and drives upper sliders 11, lower sliders 22 and the sealing ring 3 to splay outward, thereby facilitating the inserting of the surgical instrument 8. Meanwhile, a straight notch of the straight silica gel sealing ring is pushed open by the surgical instrument, so the surgical instrument can be inserted in a body cavity.

When the surgical instrument 8 is removed, the lower sliders 22 of a lower guiding mechanism 2 have the guiding effect and facilitate the removing of the surgical instrument, and under the effect of the elastic resilience of the sealing ring 3, the sealing ring 3 restores to the initial state without the inserting of the surgical instrument, that is, the surgical instrument through hole 31 of the sealing ring restores to the initial diameter, and meanwhile, the upper sliders 11 and the lower sliders 22 also restore to the initial position without the inserting of the surgical instrument. Meanwhile, the straight notch of the sealing ring closes automatically under the effect the elastic resilience of silica gel, thereby having the effect of axial sealing and preventing the leakage of $CO_2$ gas.

Embodiment 12: A trocar adopting a rotation shaft type connection mechanism according to the present invention Referring to FIG. 13-1 to FIG. 13-2, the difference of this embodiment from Embodiment 11 lies in that: in this embodiment, a dynamic connection mechanism 112 adopts an axial limit rotation mechanism, a rotation shaft 1122 is disposed on the upper side of a upper guiding mechanism 1 and forms a shaft limit rotation mechanism with a shaft positioning groove 1124 on a positioning block 52 of the trocar, so as to serve as a dynamic connection mechanism 4.

After a surgical instrument 8 is inserted, the rotation shaft 1122 rotates and drives upper sliders 11, lower sliders 22 and a sealing ring 3 to splay outward, thereby facilitating the inserting of the surgical instrument 8. Meanwhile, a straight notch of the straight silica gel sealing ring is pushed open by the surgical instrument, so the surgical instrument can be inserted in a body cavity.

When the surgical instrument 8 is removed, the lower sliders 22 on the lower guiding mechanism 2 have the guiding effect and facilitate the removing of the surgical instrument, and under the effect of the elastic resilience of the sealing ring 3, the sealing ring 3 restores to the initial state without the inserting of the surgical instrument, that is, a surgical instrument through hole 31 of the sealing ring restores to the initial diameter, and meanwhile, the upper sliders 11 and the lower sliders 22 also restore to the initial position without the inserting of the surgical instrument. Meanwhile, the straight notch of the sealing ring closes automatically under the effect of elastic resilience of silica gel, thereby having the effect of axial sealing and preventing the leakage of $CO_2$ gas.

Additionally, a radial sealing ring of the trocar of the present invention may adopt a low-resistance general sealing apparatus 7 of the present invention; while a check valve 9, or referred to as an axial sealing apparatus, adopts a flipping-type sealing apparatus. In the trocar of the present invention adopting the combination, when no surgical instrument is inserted, a spring of the flipping-type sealing apparatus oppresses the silica gel sealing ring of the flipping-type sealing apparatus to prevent the leakage of $CO_2$ gas.

When the surgical instrument is inserted, the surgical instrument 8 is inserted along the upper guiding mechanism 1, the upper sliders 11 splay outward, gaps 13 between the upper sliders 11 gradually enlarge, and the lower part of the sealing ring 3 deforms, while the surgical instrument through hole 31 of the sealing ring surrounds the surgical instrument 8 to form radial sealing. Meanwhile, the flipper is pushed open by the surgical instrument, so the surgical instrument can be inserted in a body cavity.

When the surgical instrument is removed, the surgical instrument 8 removes gradually along the lower guiding mechanism 2, the lower sliders 21 contract centripetally gradually under the effect of the elastic resilience of the sealing ring 3, the gaps 13 reduce gradually, and when the instrument is completely removed, the surgical instrument through hole 31 of the sealing ring completely restores to the initial state. Meanwhile, the spring of the flipping-type sealing apparatus oppresses the silica gel sealing ring of the flipping-type sealing apparatus to close the axial check valve again to prevent the leakage of $CO_2$ gas.

The trocar of the present invention may further selects a spherical sealing apparatus as the check valve 9, and the low-resistance general sealing apparatus of the present invention, as a radial sealing apparatus 7, is mounted in a sheath of the trocar.

It should be pointed out that, a magnet may be mounted in the upper guiding mechanism 1 of the sealing apparatus of the present invention and a hollow sphere may be made of a ferromagnetic material. Under the attraction of the magnetic force, the sphere and the surgical instrument through hole 31 of the sealing ring of the sealing apparatus of the present invention form axial sealing, namely, the check valve 9.

When the surgical instrument is inserted, the surgical instrument 8 is inserted along the upper guiding mechanism 1, the upper sliders 11 splay outward, the gaps 13 between the upper sliders 11 gradually enlarge, and the lower part of the sealing ring 3 deforms, while the surgical instrument through hole 31 surrounds the surgical instrument 8 of the sealing ring to form radial sealing. Meanwhile, the hollow sphere is pushed open by the surgical instrument, so the surgical instrument can be inserted in a body cavity.

When the surgical instrument is removed, the surgical instrument 8 removes gradually along the lower guiding mechanism 2, the lower sliders 21 contract centripetally gradually under the effect of the elastic resilience of the sealing ring 3 and the gaps 13 reduce gradually. When the instrument is completely removed, the surgical instrument through hole 31 of the sealing ring completely restores to the initial state. Meanwhile, the hollow sphere blocks the surgical instrument through hole 31 of the sealing ring under the effect of magnetic force, thereby having the effect of axial sealing and preventing the leakage of $CO_2$ gas.

Additionally, a trocar rod used by the trocar the present invention may be a trocar rod with a protection cutterhead, or may be a trocar rod without a protection cutterhead, such as a triangular blade trocar rod, a conical blunt trocar rod and a blunt trocar rod with flanks.

It should be noted that, the structures disclosed and illustrated in the specification may be replaced by other structures with the same effect, and meanwhile, the embodiment introduced in the present invention is not the unique structure implementing the present invention. Although preferred embodiments the present invention are already introduced and introduced in the specification, but it is clearly known by persons of skill in the art that the embodiments are merely examples, and persons of skill in the art can make innumerable changes, improvement and replacement without departing from the present invention. Therefore, the protection scope of the present invention shall be limited according to the spirit and scope of claims accompanied by the present invention.

While particular embodiments are described above, it will be understood it is not intended to limit the invention to these particular embodiments. On the contrary, the invention includes alternatives, modifications and equivalents that are within the spirit and scope of the appended claims. Numerous specific details are set forth in order to provide a thorough understanding of the subject matter presented herein. But it will be apparent to one of ordinary skill in the art that the subject matter may be practiced without these specific details. In other instances, well-known methods, procedures, components, and circuits have not been described in detail so as not to unnecessarily obscure aspects of the embodiments.

Although the terms first, second, etc. may be used herein to describe various elements, these elements should not be limited by these terms. These terms are only used to distinguish one element from another. For example, first ranking criteria could be termed second ranking criteria, and, similarly, second ranking criteria could be termed first ranking criteria, without departing from the scope of the present invention. First ranking criteria and second ranking criteria are both ranking criteria, but they are not the same ranking criteria.

The terminology used in the description of the invention herein is for the purpose of describing particular embodiments only and is not intended to be limiting of the invention. As used in the description of the invention and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, operations, elements, and/or components, but do not preclude the presence or addition of one or more other features, operations, elements, components, and/or groups thereof.

As used herein, the term "if" may be construed to mean "when" or "upon" or "in response to determining" or "in accordance with a determination" or "in response to detecting," that a stated condition precedent is true, depending on the context. Similarly, the phrase "if it is determined [that a stated condition precedent is true]" or "if [a stated condition precedent is true]" or "when [a stated condition precedent is true]" may be construed to mean "upon determining" or "in response to determining" or "in accordance with a determination" or "upon detecting" or "in response to detecting" that the stated condition precedent is true, depending on the context.

Although some of the various drawings illustrate a number of logical stages in a particular order, stages that are not order dependent may be reordered and other stages may be combined or broken out. While some reordering or other groupings are specifically mentioned, others will be obvious to those of ordinary skill in the art and so do not present an exhaustive list of alternatives. Moreover, it should be recognized that the stages could be implemented in hardware, firmware, software or any combination thereof.

The foregoing description, for purpose of explanation, has been described with reference to specific implementations. However, the illustrative discussions above are not intended to be exhaustive or to limit the invention to the precise forms disclosed. Many modifications and variations are possible in view of the above teachings. The implementations were chosen and described in order to best explain principles of the invention and its practical applications, to thereby enable others skilled in the art to best utilize the invention and various implementations with various modifications as are suited to the particular use contemplated. Implementations include alternatives, modifications and equivalents that are within the spirit and scope of the appended claims. Numerous specific details are set forth in order to provide a thorough understanding of the subject matter presented herein. But it will be apparent to one of ordinary skill in the art that the subject matter may be practiced without these specific details. In other instances, well-known methods, procedures, components, and circuits have not been described in detail so as not to unnecessarily obscure aspects of the implementations.

What is claimed is:

1. A low-resistance general sealing apparatus for a trocar, comprising an upper guiding mechanism, a lower guiding mechanism, a sealing ring and a connection locking mechanism, wherein
   the upper guiding mechanism is provided with two or more upper sliders, a funnel-shaped structure having a large upper part and a small lower part is formed between the upper sliders, and each upper slider is provided with a respective first guiding surface;
   the lower guiding mechanism is provided with two or more lower sliders, an inverted funnel-shaped structure having a small upper part and a large lower part is formed between the lower sliders, and each lower slider is provided with a respective second guiding surface;
   the sealing ring is made of an elastic medical macromolecular material and is provided with a surgical instrument through hole and a plurality of locking through holes;
   the connection locking mechanism is a concave-convex matching structure including a plurality of pairs of convex lock pin and concave lock slot, and each pair of convex lock pin and concave lock slot is configured to fix the upper guiding mechanism onto the lower guiding mechanism with the sealing ring positioned between the upper guiding mechanism and the lower guiding mechanism via a corresponding locking through hole therein;
   a smooth transition is formed between the upper sliders and the corresponding lower sliders; and
   the diameter of the surgical instrument through hole in the sealing ring is smaller than the diameter of a lower through hole of the upper guiding mechanism and the diameter of an upper through hole of the lower guiding mechanism.

2. The low-resistance general sealing apparatus for a trocar according to claim 1, wherein the connection locking mechanism is configured to fix the upper guiding mechanism onto the lower guiding mechanism through a clip-based concave-convex matching mechanism; or, the connection locking mechanism is configured to fix the upper guiding mechanism onto the lower guiding mechanism through the concave-convex match structure by applying a heat seal or welding technique to the upper guiding mechanism and the lower guiding mechanism; or, the connection locking mechanism is configured to fix the upper guiding mechanism onto the lower guiding mechanism through the concave-convex match structure by applying a chemical binder to the upper guiding mechanism and the lower guiding mechanism.

3. The low-resistance general sealing apparatus for a trocar according to claim 1, wherein the upper guiding mechanism is provided with a dynamic connection mechanism.

4. The low-resistance general sealing apparatus for a trocar according to claim 3, wherein the dynamic connection mechanism refers to a low-resistance area formed by a groove or an elastic material that easily deforms under an external force and restores its original shape after the external force of deformation is removed; or, the dynamic connection mechanism refers to a movable spherical or axial limit rotation mechanism.

5. The low-resistance general sealing apparatus for a trocar according to claim 1, wherein the diameter of the lower through hole of the funnel-shaped structure having a large upper part and a small lower part formed between the upper sliders is close or equal to the diameter of the upper through hole of the inverted funnel-shaped structure having a small upper part and a large lower part formed between the lower sliders.

6. The low-resistance general sealing apparatus for a trocar according to claim 1, wherein a structure of the upper guiding mechanism is a 4-segment funnel-shaped structure having a large upper part and a small lower part and formed by 4 upper sliders; and a structure of the lower guiding mechanism is a 4-segment inverted funnel-shaped structure having a small upper part and a large lower part and formed by 4 lower sliders matched with the upper sliders.

7. The low-resistance general sealing apparatus for a trocar according to claim 6, wherein, among the 4 upper sliders forming the upper guiding mechanism, a first set of 2 upper sliders forms a pair of primary guiding gliders, and a second set of 2 upper sliders forms a pair of auxiliary guiding gliders, wherein the primary guiding gliders and the auxiliary guiding gliders have different colors, and wherein a respective size of the respective first guiding surface of the first set of 2 upper sliders is greater than a respective size of the respective first guiding surface of the second set of 2 upper sliders.

8. The low-resistance general sealing apparatus for a trocar according to claim 1, wherein the sealing ring is a sealing ring having a trapezoidal, quasi-trapezoidal, V-shaped or approximately H-shaped cross section.

9. The low-resistance general sealing apparatus for a trocar according to claim 8, wherein when the sealing ring is a sealing ring having a trapezoidal or quasi-trapezoidal cross section, the diameter $D_{31}$ of the surgical instrument through hole is between 1 mm and 5 mm; the diameter $D_{32}$ of the bottom of the trapezoidal sealing ring is between 3 mm and 40 mm; and the thickness $\delta$ of the bottom of the trapezoidal sealing ring is between 0.05 mm and 1.5 mm.

10. The low-resistance general sealing apparatus for a trocar according to claim 9, wherein a wall thickness of the sealing ring varies throughout the sealing ring.

11. The low-resistance general sealing apparatus for a trocar according to claim 1, wherein an angle $\beta$ between the respective first guiding surface of the upper guiding mechanism and a central shaft of the funnel-shaped structure is between 80° and 10°.

12. The low-resistance general sealing apparatus for a trocar according to claim 1, wherein the sealing ring is provided with a buffering ring, and the buffering ring is of a wrinkle structure.

13. The low-resistance general sealing apparatus for a trocar according to claim 1, wherein the upper guiding mechanism is fixed on the upper side of the sealing ring through the concave-convex structure.

14. The low-resistance general sealing apparatus for a trocar according to claim 1, wherein the sealing apparatus is provided with a positioning block used to fix the sealing ring and/or the dynamic connection mechanism of the upper guiding mechanism.

15. The low-resistance general sealing apparatus for a trocar according to claim 1, wherein the lower end of the lower slider of the lower guiding mechanism is provided with a traction plate, and the traction plate is made of an elastic medical macromolecular material selected from medical silica gel, medical rubber, medical polyurethane, medical latex and a combination thereof.

16. A trocar, comprising the low-resistance sealing apparatus for a trocar according to claim 1.

17. The trocar according to claim 16, wherein the low-resistance general sealing apparatus of the trocar is mounted, through a dynamic connection mechanism, on a housing of a sheath of the trocar or on a positioning block.

18. The trocar according to claim 16, wherein a radial sealing of the trocar adopts the low-resistance general sealing apparatus according to claim 1 and an axial sealing adopts a funnel-shaped straight sealing ring.

19. The trocar according to claim 16, wherein a radial sealing of the trocar adopts the low-resistance general sealing apparatus according to claim 1 and an axial sealing adopts a flipping-type sealing apparatus.

20. The trocar according to claim 16, wherein a radial sealing of the trocar adopts the low-resistance general sealing apparatus according to claim 1 and an axial sealing adopts a spherical sealing apparatus.

* * * * *